(12) United States Patent
Raslambekov

(10) Patent No.: US 11,197,744 B1
(45) Date of Patent: Dec. 14, 2021

(54) METHOD AND SYSTEM FOR GENERATING INTERDENTAL FILLER MODELS

(71) Applicant: Oxilio Ltd, Larnaca (CY)

(72) Inventor: Islam Khasanovich Raslambekov, Long Island City, NY (US)

(73) Assignee: ARKIMOS Ltd, Larnaca (CY)

( * ) Notice: Subject to any disclaimer, the term of this patent is extended or adjusted under 35 U.S.C. 154(b) by 0 days.

(21) Appl. No.: 17/143,033

(22) Filed: Jan. 6, 2021

(51) Int. Cl.
| | |
|---|---|
| *A61C 13/00* | (2006.01) |
| *A61C 7/00* | (2006.01) |
| *G06F 30/10* | (2020.01) |
| *G06T 11/20* | (2006.01) |
| *G06F 30/20* | (2020.01) |
| *G06F 30/00* | (2020.01) |
| *A61C 7/08* | (2006.01) |
| *G06T 11/40* | (2006.01) |
| *G16H 10/60* | (2018.01) |

(52) U.S. Cl.
CPC .......... *A61C 13/0004* (2013.01); *A61C 7/002* (2013.01); *G06F 30/10* (2020.01); *G06F 30/20* (2020.01); *G06T 11/203* (2013.01); *G16H 10/60* (2018.01); *A61C 7/08* (2013.01); *A61C 2007/004* (2013.01); *G06F 30/00* (2020.01); *G06T 11/40* (2013.01)

(58) Field of Classification Search
CPC ............................ A61C 13/0004; A61C 7/002
See application file for complete search history.

(56) References Cited

U.S. PATENT DOCUMENTS

| | | | |
|---|---|---|---|
| 4,867,683 | A | 9/1989 | Meisel |
| 4,875,856 | A | 10/1989 | Grussmark |
| 5,888,068 | A | 3/1999 | Lans et al. |
| 5,975,893 | A | 11/1999 | Chishti et al. |
| 6,183,248 | B1 | 2/2001 | Chishti et al. |
| 6,227,850 | B1 | 5/2001 | Chishti et al. |
| 6,309,215 | B1 | 10/2001 | Phan et al. |
| 6,318,994 | B1 | 11/2001 | Chishti et al. |
| 6,334,853 | B1 | 1/2002 | Kopelman et al. |
| 6,386,878 | B1 | 5/2002 | Pavlovskaia et al. |
| 6,398,548 | B1 | 6/2002 | Muhammad et al. |
| 6,463,344 | B1 | 10/2002 | Pavloskaia et al. |
| 6,471,511 | B1 | 10/2002 | Chishti et al. |
| 6,554,611 | B2 | 4/2003 | Chishti et al. |
| 6,602,070 | B2 | 8/2003 | Miller et al. |

(Continued)

FOREIGN PATENT DOCUMENTS

| | | |
|---|---|---|
| RU | 2231331 C1 | 6/2004 |
| RU | 2698998 C1 | 9/2019 |

(Continued)

*Primary Examiner* — Akash Saxena
(74) *Attorney, Agent, or Firm* — BCF LLP

(57) ABSTRACT

Methods, systems, and apparatuses are described for generating an interdental filler model for a patient. Locations for ends of the interdental filler model may be determined. A curvature of the interdental filler model may be determined. A shape of the interdental filler model may be determined. A first arc may be determined for a first end of the interdental filler model and a second arc may be determined for a second end of the interdental filler model. A set of arcs may be interpolated between the first arc and the second arc. The set of arcs may be grounded on the patient's gingiva. The interdental filler model may be generated based on the set of arcs.

20 Claims, 24 Drawing Sheets

(56) References Cited

U.S. PATENT DOCUMENTS

| | | | |
|---|---|---|---|
| 6,665,570 B2 | 12/2003 | Pavloskaia et al. | |
| 6,685,470 B2 * | 2/2004 | Chishti | A61C 7/00 433/24 |
| 6,688,886 B2 | 2/2004 | Hughes et al. | |
| 6,694,212 B1 | 2/2004 | Kennedy | |
| 6,702,575 B2 | 3/2004 | Hilliard | |
| 6,705,863 B2 | 3/2004 | Phan et al. | |
| 6,726,478 B1 | 4/2004 | Isiderio et al. | |
| 6,739,870 B2 | 5/2004 | Lai et al. | |
| 6,767,208 B2 | 7/2004 | Kaza | |
| 6,790,035 B2 | 9/2004 | Tricca et al. | |
| 6,979,196 B2 | 12/2005 | Nikolskiy et al. | |
| 7,040,896 B2 | 5/2006 | Pavlovskaia et al. | |
| 7,059,850 B1 | 6/2006 | Phan et al. | |
| 7,063,532 B1 | 6/2006 | Jones et al. | |
| 7,123,767 B2 | 10/2006 | Jones et al. | |
| 7,125,248 B2 | 10/2006 | Phan et al. | |
| 7,134,874 B2 | 11/2006 | Chishti et al. | |
| 7,220,122 B2 | 5/2007 | Chishti | |
| 7,241,142 B2 | 7/2007 | Abolfathi et al. | |
| 7,255,561 B2 | 8/2007 | Tricca et al. | |
| 7,293,988 B2 | 11/2007 | Wen | |
| 7,320,592 B2 | 1/2008 | Chishti et al. | |
| 7,373,286 B2 | 5/2008 | Nikolskiy et al. | |
| 7,377,778 B2 | 5/2008 | Chishti et al. | |
| 7,428,481 B2 | 9/2008 | Nikolskiy et al. | |
| 7,442,040 B2 | 10/2008 | Kuo | |
| 7,637,740 B2 | 12/2009 | Knopp | |
| 7,689,398 B2 | 3/2010 | Cheng et al. | |
| 7,711,447 B2 * | 5/2010 | Lu | G16Z 99/00 700/187 |
| 7,771,195 B2 | 8/2010 | Knopp et al. | |
| 7,826,646 B2 | 11/2010 | Pavlovskaia et al. | |
| 7,841,858 B2 | 11/2010 | Knopp et al. | |
| 7,844,429 B2 | 11/2010 | Matov et al. | |
| 7,865,259 B2 | 1/2011 | Kuo et al. | |
| 7,904,307 B2 | 3/2011 | Abolfathi et al. | |
| 7,905,725 B2 | 3/2011 | Chishti et al. | |
| 7,942,672 B2 | 5/2011 | Kuo | |
| 7,993,134 B2 | 8/2011 | Wen | |
| 8,038,444 B2 | 10/2011 | Kitching et al. | |
| 8,044,954 B2 | 10/2011 | Kitching et al. | |
| 8,108,189 B2 | 1/2012 | Chelnokov et al. | |
| 8,131,393 B2 | 3/2012 | Matov et al. | |
| 8,135,569 B2 | 3/2012 | Matov et al. | |
| 8,244,390 B2 | 8/2012 | Kuo et al. | |
| 8,393,897 B2 | 3/2013 | Clark et al. | |
| 8,401,826 B2 | 3/2013 | Cheng et al. | |
| 8,439,672 B2 | 5/2013 | Matov et al. | |
| 8,465,280 B2 | 6/2013 | Sachdeva et al. | |
| 8,478,435 B2 | 7/2013 | Kuo et al. | |
| 8,639,477 B2 | 1/2014 | Chelnokov et al. | |
| 8,641,414 B2 | 2/2014 | Borovinskih et al. | |
| 8,734,150 B2 | 5/2014 | Wen | |
| 8,780,106 B2 | 7/2014 | Chishti et al. | |
| 8,807,999 B2 | 8/2014 | Kuo et al. | |
| 8,896,592 B2 | 11/2014 | Boltunov et al. | |
| 8,897,902 B2 | 11/2014 | See et al. | |
| 8,961,173 B2 | 2/2015 | Miller | |
| 9,060,829 B2 | 6/2015 | Sterental et al. | |
| 9,107,722 B2 | 8/2015 | Matov et al. | |
| 9,161,823 B2 | 10/2015 | Morton et al. | |
| 9,211,166 B2 | 12/2015 | Kuo et al. | |
| 9,326,831 B2 | 5/2016 | Cheang | |
| 9,345,557 B2 | 5/2016 | Anderson et al. | |
| 9,375,293 B2 | 6/2016 | Taub et al. | |
| 9,375,300 B2 | 6/2016 | Matov et al. | |
| 9,414,897 B2 | 8/2016 | Wu et al. | |
| 9,433,476 B2 | 9/2016 | Khardekar et al. | |
| 9,529,970 B2 | 12/2016 | Andreiko | |
| 9,592,103 B2 | 3/2017 | Taub et al. | |
| 9,610,140 B2 | 4/2017 | Anderson et al. | |
| 9,622,834 B2 | 4/2017 | Chapoulaud et al. | |
| 9,767,223 B2 | 9/2017 | Fisker et al. | |
| 9,792,413 B2 | 10/2017 | Badawi | |
| 9,844,424 B2 | 12/2017 | Wu et al. | |
| 10,011,050 B2 | 7/2018 | Kitching et al. | |
| 10,076,389 B2 | 9/2018 | Wu et al. | |
| 10,123,852 B2 | 11/2018 | Kuo | |
| 10,307,222 B2 | 6/2019 | Morton et al. | |
| 10,332,164 B2 | 6/2019 | Abolfathi et al. | |
| 10,383,704 B2 | 8/2019 | Kitching | |
| 10,405,947 B1 | 9/2019 | Kaza et al. | |
| 10,405,951 B1 | 9/2019 | Kopelman et al. | |
| 10,413,385 B2 | 9/2019 | Sherwood et al. | |
| 10,426,578 B2 * | 10/2019 | Rubbert | A61C 13/0028 |
| 10,433,934 B2 | 10/2019 | Kopelman | |
| 10,463,452 B2 | 11/2019 | Matov et al. | |
| 10,470,846 B2 | 11/2019 | Kopelman et al. | |
| 10,524,880 B2 | 1/2020 | Wen | |
| 10,531,939 B2 | 1/2020 | Stotland et al. | |
| 10,553,309 B2 | 2/2020 | Trosien et al. | |
| 10,561,476 B2 | 2/2020 | Matov et al. | |
| 10,595,965 B2 | 3/2020 | Khardekar et al. | |
| 10,613,515 B2 | 4/2020 | Cramer et al. | |
| 10,617,489 B2 | 4/2020 | Grove et al. | |
| 10,650,517 B2 | 5/2020 | Parpara et al. | |
| 10,653,503 B2 | 5/2020 | Boltunov et al. | |
| 10,706,184 B2 * | 7/2020 | Fisker | A61C 13/0004 |
| 10,722,328 B2 | 7/2020 | Velazquez et al. | |
| 10,783,629 B2 | 9/2020 | Parpara et al. | |
| 10,792,127 B2 | 10/2020 | Kopelman et al. | |
| 10,813,721 B2 | 10/2020 | Sterental et al. | |
| 10,950,061 B1 * | 3/2021 | Raslambekov | G16H 10/60 |
| 2004/0081938 A1 * | 4/2004 | Chishti | A61C 7/00 433/24 |
| 2005/0244791 A1 | 11/2005 | Davis et al. | |
| 2006/0105294 A1 * | 5/2006 | Burger | A61C 13/0004 433/167 |
| 2008/0154419 A1 * | 6/2008 | Cheng | G06T 7/60 700/118 |
| 2009/0053677 A1 * | 2/2009 | Orth | A61C 13/0006 433/215 |
| 2013/0095446 A1 | 4/2013 | Andreiko et al. | |
| 2014/0288894 A1 | 9/2014 | Chishti et al. | |
| 2015/0056576 A1 * | 2/2015 | Nikolskiy | A61C 9/004 433/214 |
| 2016/0302885 A1 | 10/2016 | Matov et al. | |
| 2017/0035536 A1 | 2/2017 | Alvarez Garcia et al. | |
| 2017/0079748 A1 | 3/2017 | Andreiko | |
| 2017/0156827 A1 | 6/2017 | Carter et al. | |
| 2018/0039755 A1 | 2/2018 | Matov et al. | |
| 2018/0165818 A1 | 6/2018 | Tsai et al. | |
| 2018/0304497 A1 | 10/2018 | Kitching et al. | |
| 2019/0000592 A1 | 1/2019 | Cam et al. | |
| 2019/0046295 A1 | 2/2019 | Morton et al. | |
| 2019/0105127 A1 * | 4/2019 | Velazquez | A61C 7/08 |
| 2019/0105128 A1 * | 4/2019 | Velazquez | G06T 17/20 |
| 2019/0105130 A1 * | 4/2019 | Grove | A61C 1/082 |
| 2019/0152152 A1 * | 5/2019 | O'Leary | B33Y 50/00 |
| 2019/0282333 A1 | 9/2019 | Matov et al. | |
| 2019/0314117 A1 | 10/2019 | Morton et al. | |
| 2019/0357997 A1 | 11/2019 | Shi et al. | |
| 2020/0000551 A1 | 1/2020 | Li et al. | |
| 2020/0000552 A1 | 1/2020 | Mednikov et al. | |
| 2020/0100863 A1 | 4/2020 | Kirchner et al. | |
| 2020/0146776 A1 | 5/2020 | Matov et al. | |
| 2020/0155274 A1 | 5/2020 | Pimenov et al. | |
| 2020/0229900 A1 | 7/2020 | Cunliffe et al. | |
| 2020/0246114 A1 | 8/2020 | Clark | |
| 2020/0289239 A1 * | 9/2020 | Raby | B29C 64/386 |
| 2020/0297459 A1 | 9/2020 | Grove et al. | |
| 2020/0306012 A1 | 10/2020 | Roschin et al. | |
| 2020/0397537 A1 * | 12/2020 | Raby | B29C 64/393 |

FOREIGN PATENT DOCUMENTS

| | | | |
|---|---|---|---|
| WO | 98058596 A1 | 12/1998 | |
| WO | WO/2000/019928 | * 10/1999 | A61C 7/00 |
| WO | 00019928 A1 | 4/2000 | |
| WO | 00019930 A1 | 4/2000 | |
| WO | 00019931 A1 | 4/2000 | |
| WO | 00069356 A1 | 11/2000 | |

(56) References Cited

FOREIGN PATENT DOCUMENTS

| WO | 00069357 | A1 | 11/2000 |
| WO | 01074268 | A1 | 11/2001 |
| WO | 2018085718 | A2 | 5/2018 |
| WO | 2019089989 | A2 | 5/2019 |

* cited by examiner

METHOD AND SYSTEM FOR GENERATING INTERDENTAL FILLER MODELS

FIELD

The present technology relates to generating interdental filler models configured to fill interdental gaps between patients' teeth.

BACKGROUND

An orthodontic treatment plan may be created for a patient. The orthodontic treatment plan may include an orthodontic appliance, such as an aligner, to be worn by the patient.

The patient may have interdental gaps between some of their teeth. For example, an interdental gap may exist where the patient has previously lost a tooth. Interdental gaps may cause the patient discomfort when the patient wears an orthodontic appliance. Interdental gaps may decrease the effectiveness of the orthodontic appliance.

SUMMARY

It is an object of the present technology to ameliorate at least some of the inconveniences present in the prior art.

Embodiments of the present technology have been developed based on developers' appreciation that interdental fillers may be used to fill interdental gaps between a patient's teeth. Systems and/or methods for generating interdental filler models may be beneficial when planning an orthodontic treatment for the patient, using for example automated or semi-automated orthodontic treatment planners. Systems and/or methods for generating interdental filler models may also be used for manufacturing aligners for patients with interdental gaps.

Embodiments of the present technology have been developed based on developers' appreciation that the use of interdental fillers may reduce a patient's discomfort when using an orthodontic appliance. Embodiments of the present technology have been developed based on developers' appreciation that the use of interdental fillers may increase the effectiveness of an orthodontic appliance, such as by providing additional support and/or reducing bending or any other deformation of the orthodontic appliance.

According to one aspect, there is provided a method for generating an interdental filler model for a patient, wherein the interdental filler model is configured to fill an interdental gap between a first tooth and a second tooth of the patient, wherein the first tooth and the second tooth are neighboring teeth, the method executable by a processor of a computing system, the method comprising: receiving a three-dimensional (3D) digital model of an archform of the patient, wherein the 3D digital model comprises a representation of gingiva and a plurality of teeth including the first tooth and the second tooth; determining locations for ends of the interdental filler model by: determining a first vertex on a tooth axis of the first tooth, and determining a second vertex on a tooth axis of the second tooth; determining a curvature of the interdental filler model by: determining a first arc connecting the first vertex to the second vertex; determining a shape of the interdental filler model by: determining a second arc having a center at the first vertex, determining a third arc having a center at the second vertex, and interpolating a set of arcs between the second arc and the third arc, wherein a center of each arc in the set of arcs is a vertex on the first arc; grounding the interdental filler model on the gingiva by: extending each arc of the set of arcs to end on a ground surface; and generating the interdental filler model by: connecting free ends of each arc of the set of arcs, thereby forming a set of sections, lofting each section of the set of sections, and forming the interdental filler model based on the set of sections.

In certain embodiments, determining the locations for ends of the interdental filler model comprises: determining a third vertex corresponding to the first tooth; determining a fourth vertex corresponding to the second tooth; and determining a center point of a line connecting the third vertex and the fourth vertex, wherein the first arc comprises the center point.

In certain embodiments, determining the first vertex comprises determining a nearest vertex on the tooth axis of the first tooth to the center point.

In certain embodiments, determining the third vertex comprises determining a highest or lowest vertex of the first tooth.

In certain embodiments, determining the shape of the interdental filler model comprises: determining, based on the tooth axis of the first tooth, a first plane comprising the first vertex; determining, based on the tooth axis of the second tooth, a second plane comprising the second vertex; determining a first intersection curve, wherein the first intersection curve comprises a boundary line between the first tooth and the first plane; determining a second intersection curve, wherein the second intersection curve comprises a boundary line between the second tooth and the second plane; determining a first distance from a point on the first intersection curve to the first vertex; and determining a second distance from a point on the second intersection curve to the second vertex.

In certain embodiments, the second arc has a radius less than the first distance, and wherein the third arc has a radius less than the second distance.

In certain embodiments, the method further comprises determining a tangent vector to the first arc at the first vertex.

In certain embodiments, a first axis of the first plane is a cross product of the tangent vector and the tooth axis of the first tooth.

In certain embodiments, a second axis of the first plane is the tooth axis of the first tooth.

In certain embodiments, the method further comprises manufacturing, based on the interdental filler model, an orthodontic appliance for the patient, wherein the orthodontic appliance includes a portion corresponding to the interdental filler model to fill the interdental gap between the first tooth and the second tooth.

In certain embodiments, the method further comprises manufacturing, based on the interdental filler model an interdental filler for the patient.

In certain embodiments, determining the locations for ends of the interdental filler model comprises determining the tooth axis of the first tooth and the tooth axis of the second tooth.

In certain embodiments, the method further comprises causing display of the interdental filler model.

In certain embodiments, the method further comprises superimposing the interdental filler model on the 3D digital model of the archform of the patient.

In certain embodiments, the method further comprises determining, based on a curvature of the first arc, a number of arcs to interpolate between the second arc and the third arc.

From another aspect, there is provided a system comprising: at least one processor, and memory storing a plurality of executable instructions which, when executed by the at least one processor, cause the system to: receive a three-dimensional (3D) digital model of an archform of the patient, wherein the 3D digital model comprises a representation of gingiva and a plurality of teeth including a first tooth and a second tooth that are neighboring teeth; determine locations for ends of an interdental filler model configured to fill an interdental gap between the first tooth and the second tooth by: determining a first vertex on a tooth axis of the first tooth, and determining a second vertex on a tooth axis of the second tooth; determine a curvature of the interdental filler model by: determining a first arc connecting the first vertex to the second vertex; determine a shape of the interdental filler model by: determining a second arc having a center at the first vertex, determining a third arc having a center at the second vertex, and interpolating a set of arcs between the second arc and the third arc, wherein a center of each arc in the set of arcs corresponds to a vertex on the first arc; ground the interdental filler model on the gingiva by: extending each arc of the set of arcs to end on a ground surface; and generate the interdental filler model by: connecting free ends of each arc of the set of arcs, thereby forming a set of sections, lofting each section of the set of sections, and forming the interdental filler model based on the set of sections.

In certain embodiments the instructions, when executed by the at least one processor, cause the system to manufacture, based on the interdental filler model, an orthodontic appliance for the patient, wherein the orthodontic appliance includes a portion corresponding to the interdental filler model to fill the interdental gap between the first tooth and the second tooth.

In certain embodiments the instructions, when executed by the at least one processor, cause the system to manufacture, based on the interdental filler model an interdental filler for the patient.

In certain embodiments the instructions, when executed by the at least one processor, cause the system to cause display of the interdental filler model.

In certain embodiments the instructions, when executed by the at least one processor, cause the system to superimpose the interdental filler model on the 3D digital model of the archform of the patient.

The methods, systems, and apparatuses described herein may allow a practitioner to create an interdental filler model for treating a patient. The interdental filler model may be used when creating various orthodontic appliances, such as when manufacturing an interdental filler and/or manufacturing an orthodontic appliance includes an interdental filler.

In the context of the present specification, the term "interdental filler model" refers to a 3D representation of a specific surface generated within an interdental gap between a given pair of adjacent teeth. More specifically, a given interdental filler model may extend from a distal surface of one of the given pair of adjacent teeth to a mesial surface of an other one of the given pair of adjacent teeth filling in the interdental gap therebetween. Thus, the given interdental filler model may also be referred to herein as an interdental bridge.

Further, in the context of the present specification, the term "tooth axis" of the given tooth is referred to as a line extending through the given tooth lengthwise, through a crown portion and a root portion thereof. In certain embodiments, the tooth axis is positioned such that a mass of the given tooth as well as anatomical features (such as lobes, developmental grooves, and marginal ridges thereof, for example) thereof are distributed substantially symmetrically about the tooth axis.

In the context of the present specification, unless expressly provided otherwise, a computing device and/or computer system may refer, but is not limited to, an "electronic device," an "operation system," a "system," a "computer-based system," a "controller unit," a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first," "second," "third," etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object might not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

It should be noted that, unless otherwise explicitly specified herein, the drawings are not to scale.

DETAILED DESCRIPTION

In the following description of various illustrative embodiments, reference is made to the accompanying drawings, which form a part hereof, and in which are shown, by way of illustration, various embodiments in which aspects of the disclosure may be practiced. It is to be understood that other embodiments may be utilized, and structural or functional modifications may be made, without departing from the scope of the present disclosure.

A digital model (hereinafter referred to as "model") of a patient's archform may be generated based on images and/or scans of the patient's mouth, such as images and/or scans of the teeth and gingiva of the patient. The model may comprise portions of teeth and gingiva. The model may comprise a three dimensional (3D) mesh, in which a plurality of vertices are connected to each other by edges.

Using the 3D mesh of the patient's archform, an interdental filler model may be generated for a patient. The interdental filler model may be displayed to a user, such as a practitioner designing an orthodontic appliance for the patient. The interdental filler model may be superimposed on a display of the 3D mesh of the patient's archform. The user may adjust various parameters of the interdental filler model. After adjusting the interdental filler model using the display, the user may cause an interdental filler to be produced based on the interdental filler model. Also, the interdental filler model may be used to plan an orthodontic treatment for the patient, such as for producing an orthodontic appliance based on the 3D mesh including the interdental filler.

Figure 1:
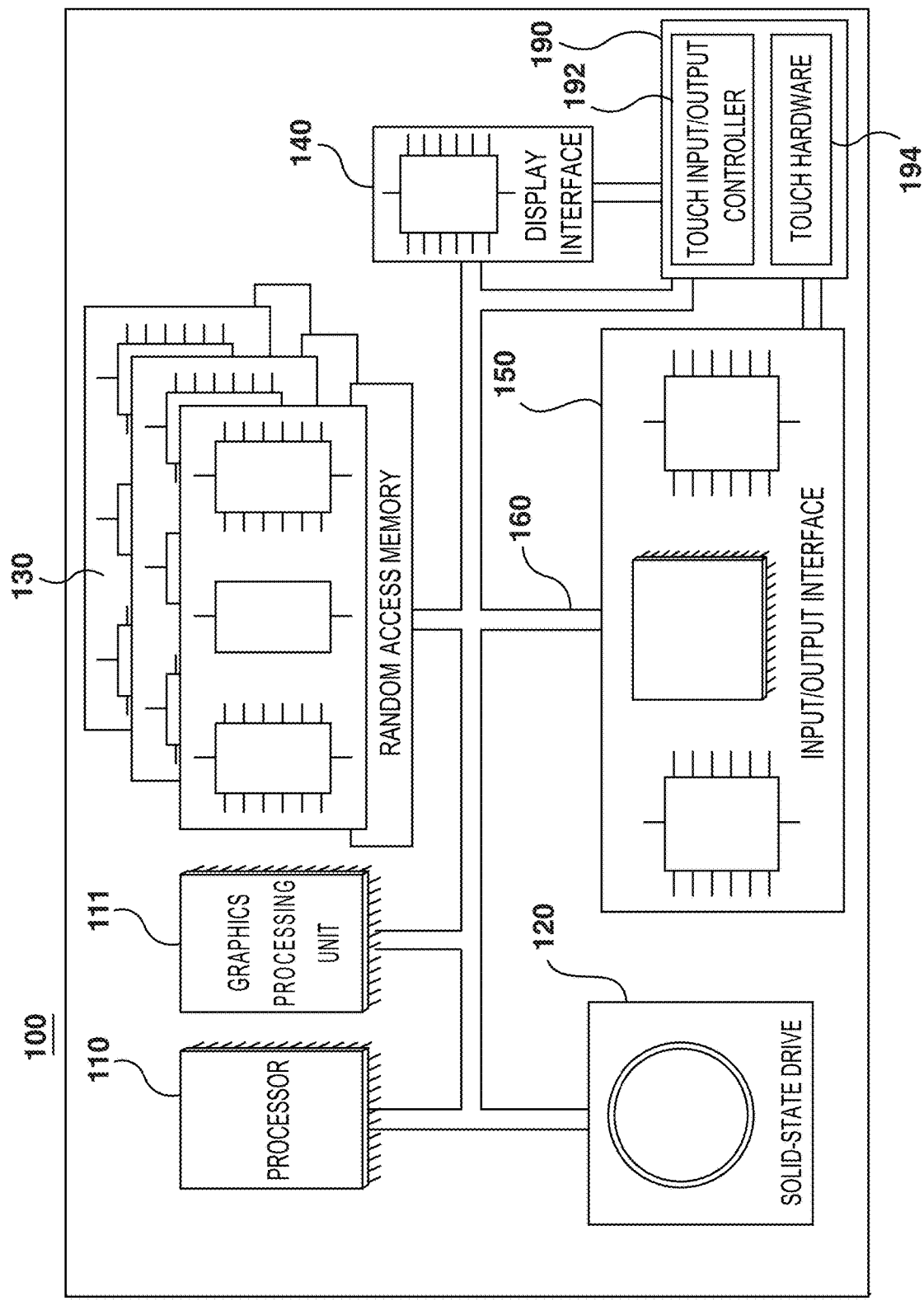
FIG. 1 is an example computer system that may be used to implement any of the methods described herein.

With reference to FIG. 1, there is shown a computer system 100 suitable for use with some implementations of the present technology. The computer system 100 may be implemented by any of a conventional personal computer, a network device and/or an electronic device (such as, but not limited to, a mobile device, a tablet device, a server, a controller unit, a control device, etc.), and/or any combination thereof appropriate to the relevant task at hand. In some embodiments, the computer system 100 comprises various hardware components including one or more single or multi-core processors collectively represented by processor 110, a solid-state drive 120, a random access memory 130, and an input/output interface 150. The computer system 100 may be a computer specifically designed to operate a machine learning algorithm (MLA). The computer system 100 may be a generic computer system.

In some embodiments, the computer system 100 may also be a subsystem of one of the above-listed systems. In some other embodiments, the computer system 100 may be an "off-the-shelf" generic computer system. In some embodiments, the computer system 100 may also be distributed amongst multiple systems. The computer system 100 may be hosted, at least partially, on a server. The computer system 100 may be partially or totally virtualized through a cloud architecture.

The computer system 100 may be specifically dedicated to the implementation of the present technology. For example, the computer system 100 may be implemented in an electronic device such as, but not limited to, a desktop computer/personal computer, a laptop, a mobile device, a smart phone, a tablet device, a server, specifically designed for managing orthodontic treatment, or for making orthodontic appliances for applying the orthodontic treatment. The computer system 100 may be configured to operate other devices, such as one or more imaging devices. As a person skilled in the art of the present technology may appreciate, multiple variations as to how the computer system 100 is implemented may be envisioned without departing from the scope of the present technology.

Those skilled in the art will appreciate that processor 110 is generally representative of a processing capability. In some embodiments, in place of or in addition to one or more conventional Central Processing Units (CPUs), one or more specialized processing cores may be provided. For example, one or more Graphic Processing Units 111 (GPUs), Tensor Processing Units (TPUs), and/or other so-called accelerated processors (or processing accelerators) may be provided in addition to or in place of one or more CPUs.

System memory will typically include random access memory 130, but is more generally intended to encompass any type of non-transitory system memory such as static random access memory (SRAM), dynamic random access memory (DRAM), synchronous DRAM (SDRAM), read-only memory (ROM), or a combination thereof. Solid-state drive 120 is shown as an example of a mass storage device, but more generally such mass storage may comprise any type of non-transitory storage device configured to store data, programs, and other information, and to make the data, programs, and other information accessible via a system bus 160. For example, mass storage may comprise one or more of a solid-state drive, hard disk drive, a magnetic disk drive, and/or an optical disk drive. The random access memory 130 and/or solid-state drive 120 may be configured in any known manner and arranged to store, among other data, one or more of: set-up data, subject data, subject medical records of one or more subjects, archform image data of the one or more of the subjects, such as 3D archform meshes, and/or orthodontic treatment data.

Communication between the various components of the computer system 100 may be enabled by a system bus 160 comprising one or more internal and/or external buses (e.g., a PCI bus, universal serial bus, IEEE 1394 "Firewire" bus, SCSI bus, Serial-ATA bus, ARINC bus, etc.), to which the various hardware components are electronically coupled.

The input/output interface 150 may provide networking capabilities such as wired or wireless access. As an example, the input/output interface 150 may comprise a networking interface such as, but not limited to, a network port, a network socket, a network interface controller and the like. Multiple examples of how the networking interface may be implemented will become apparent to the person skilled in the art of the present technology. For example, the networking interface may implement specific physical layer and data link layer standards such as Ethernet, Fibre Channel, Wi-Fi, Token Ring or Serial communication protocols. The specific physical layer and the data link layer may provide a base for a full network protocol stack, allowing communication among small groups of computers on the same local area network (LAN) and large-scale network communications through routable protocols, such as Internet Protocol (IP).

The input/output interface 150 may be coupled to a touchscreen 190 and/or to the one or more internal and/or external buses 160. The touchscreen 190 may be part of the display. In some embodiments, the touchscreen 190 is the display. The touchscreen 190 may equally be referred to as a screen 190. In the embodiments illustrated in FIG. 1, the touchscreen 190 comprises touch hardware 194 (e.g., pressure-sensitive cells embedded in a layer of a display allowing detection of a physical interaction between a user and the display) and a touch input/output controller 192 allowing communication with the display interface 140 and/or the one or more internal and/or external buses 160. In some embodiments, the input/output interface 150 may be connected to a keyboard (not shown), a mouse (not shown) or a trackpad (not shown) allowing the user to interact with the computer system 100 in addition to or instead of the touchscreen 190.

According to some implementations of the present technology, the solid-state drive 120 stores program instructions suitable for being loaded into the random access memory 130 and executed by the processor 110 for executing acts of one or more methods described herein. For example, at least some of the program instructions may be part of a library or an application.

It should be noted that the computer system 100 can be configured for receiving the image data from a vast range of devices. Some of such devices can be used for capturing and/or processing data pertaining to maxillofacial and/or cranial anatomy of the patient. In certain embodiments, the image data received from such devices is indicative of properties of anatomical structures of the patient, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of a tooth (e.g., a crown of the tooth) extending outwardly of the gingival sulcus. In some embodiments, the image data is indicative of properties of internal portions of the anatomical structures, for example volumetric properties of bone surrounding an internal portion of the tooth (e.g., a root of the tooth) extending inwardly of the gingival sulcus. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some embodiments, the image data includes datasets generally intended for the practice of periodontics.

Figure 2:
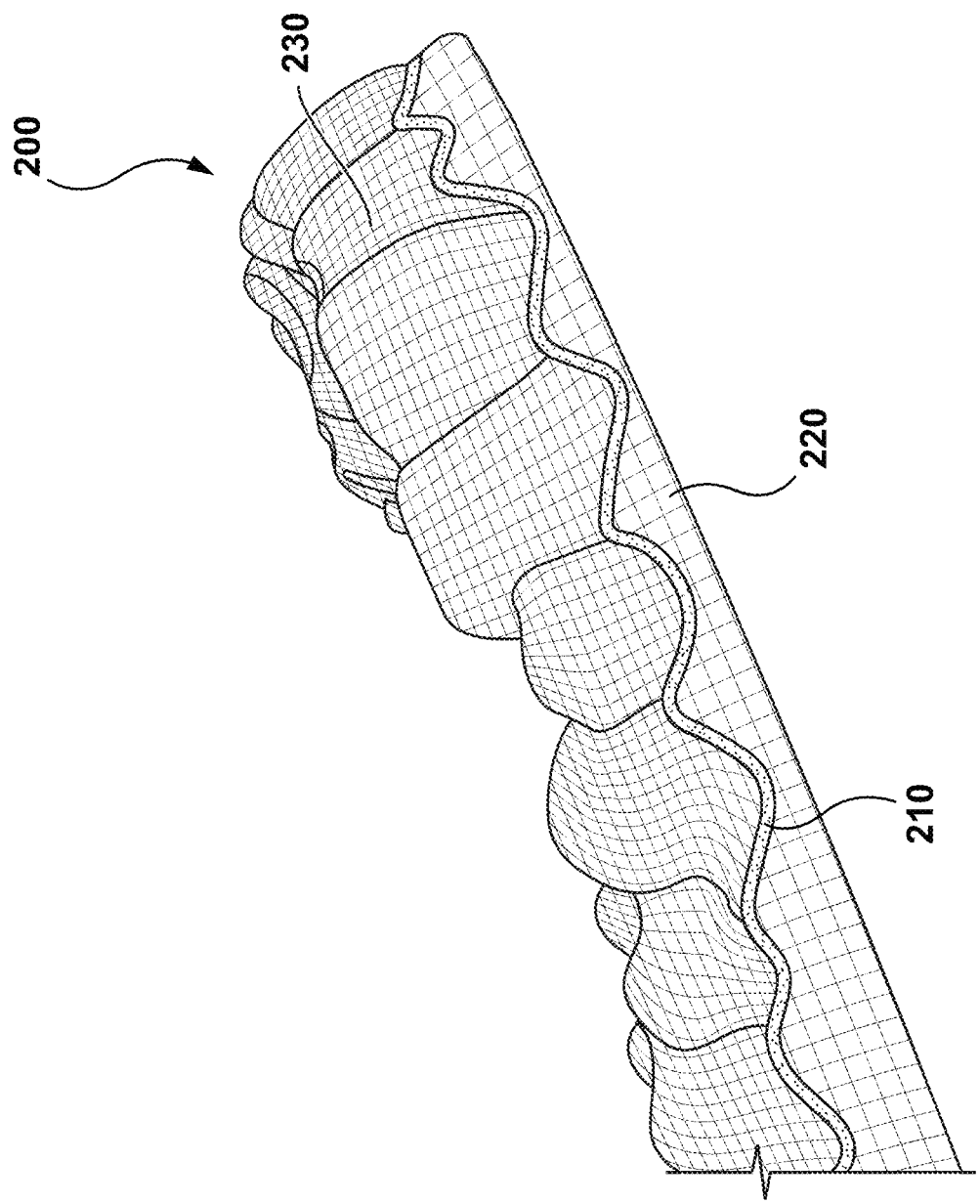
FIG. 2 shows an example of an archform mesh according to non-limiting embodiments of the present technology.

For example, in some non-limiting embodiments of the present technology, the computer system 100 may be configured to receive image data indicative of the desired configuration patient's arch form, such as an archfrom mesh 200 depicted in FIG. 2, based on the orthodontic treatment preliminarily determined for the patient. In specific non-limiting embodiments of the present technology, the orthodontic treatment may be determined, for example, by the processor 110, as described in a co-owned U.S. patent application Ser. No. 17/014,107 filed on Sep. 8, 2020, and entitled "SYSTEMS AND METHODS FOR DETERMINING A TOOTH TRAJECTORY"; a content of which is hereby incorporated by reference in its entirety.

In alternative non-limiting embodiments of the present technology, the computer system 110 may be configured to receive the image data associated with the patient directly from an imaging device (not separately depicted) communicatively coupled with the processor 110. Broadly speaking, the processor 110 may be configured to cause the imaging device may be configured to capture and/or process the image data of the patient's (such as teeth 230 depicted in FIG. 2) and the periodontium (not depicted) of the patient. In certain non-limiting embodiments of the present technology, the image data may include, for example, one or more of: (1) images of external surfaces of respective crown portions of the teeth 230, (2) images of an external surface of the periodontium including those of the patient's gingiva (such as a gingiva 220), the alveolar mandibular bone (not depicted), and images of superficial blood vessels and nerve pathways associated with the teeth 230; and (3) images of an oral region. By doing so, the imaging device may be configured, for example, to capture image data of the archform mesh 200 associated with the patient. In another example, the imaging device may also be configured to capture and/or process image data of an other archform of the patient (not depicted) associated with the patient without departing from the scope of the present technology. It should be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 430 may comprise a desktop scanner enabling to digitize a mold (not depicted) representing the desired configuration of the teeth 230, thereby generating the archform mesh 200 for the given stage of the orthodontic treatment. In this regard, the mold may have been obtained via dental impression using a material (such as a polymer, e.g. polyvinyl-siloxane) having been imprinted with the shape of the intraoral anatomy it has been applied to. In the dental impression, a flowable mixture (i.e., dental stone powder mixed with a liquid in certain proportions) may be flowed such that it may, once dried and hardened, form the replica.

In a specific non-limiting example, the desktop scanner can be of one of the types available from Dental Wings, Inc.

of 2251, ave Letourneux, Montréal (QC), Canada, H1V 2N9. It should be expressly understood that the desktop scanner can be implemented in any other suitable equipment.

Further, it is contemplated that the computer system 100 may be configured for processing of the received image data. The resulting image data of the patient's arch form received by the computer system 110 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 110 may further comprise a corresponding computing environment.

FIG. 2 shows an example of the archform mesh 200 according to non-limiting embodiments of the present technology. The archform mesh 200 is composed of vertices which are connected by edges. The archform mesh 200 represents the gingiva 220 and the teeth 230 of a patient. Although the archform mesh 200 illustrates the lower part of the patient's mouth ("lower arch"), it should be understood that an archform mesh 200 may comprise a lower and/or upper portion of the patient's mouth.

A boundary 210 separates the gingiva 220 from the teeth 230. The boundary 210 may be representative of a gumline of the patient's archform. The boundary 210 may be manually identified, or drawn, by a user (such as the dentist or the like) viewing the archform mesh 200. In some non-limiting embodiments of the present technology, the processor 110 may be configured to determine the boundary 210 automatically by analyzing the archform mesh 200. For example, the processor 110 may be configured to determine the boundary 210 using the methods and/or systems described in a co-owned U.S. Pat. No. 10,695,147-B1 issued on Jun. 30, 2020, entitled "METHOD AND SYSTEM FOR DENTAL BOUNDARY DETERMINATION", which is incorporated herein by reference.

More specifically, according to certain non-limiting embodiments of the present technology, in order to determine the boundary 210, the processor 110 may be configured to: (i) receive the archform mesh 200; (ii) define, for each tooth of the teeth 230 of the archform mesh 200, a plurality of curves, wherein each curve of the plurality of curves crosses the boundary 210 between the teeth 230 and the gingiva 220; determine, for each point of a plurality of points of each of the plurality of curves, an indication of curvature of the respective curve at each point; determine, for each point of the plurality of points and based on the indication of curvature corresponding to the respective point, a predicted likelihood parameter that each point corresponds to the boundary 210 between the teeth 230 and the gingiva 220; and select, for each curve of the plurality of curves, using a smoothing function and the predicted likelihood parameter, a single point, of the plurality of points, on the respective curve as a boundary point corresponding to the boundary 210 between the teeth 230 and the gingiva 220 of the archform mesh 200.

Figure 3:
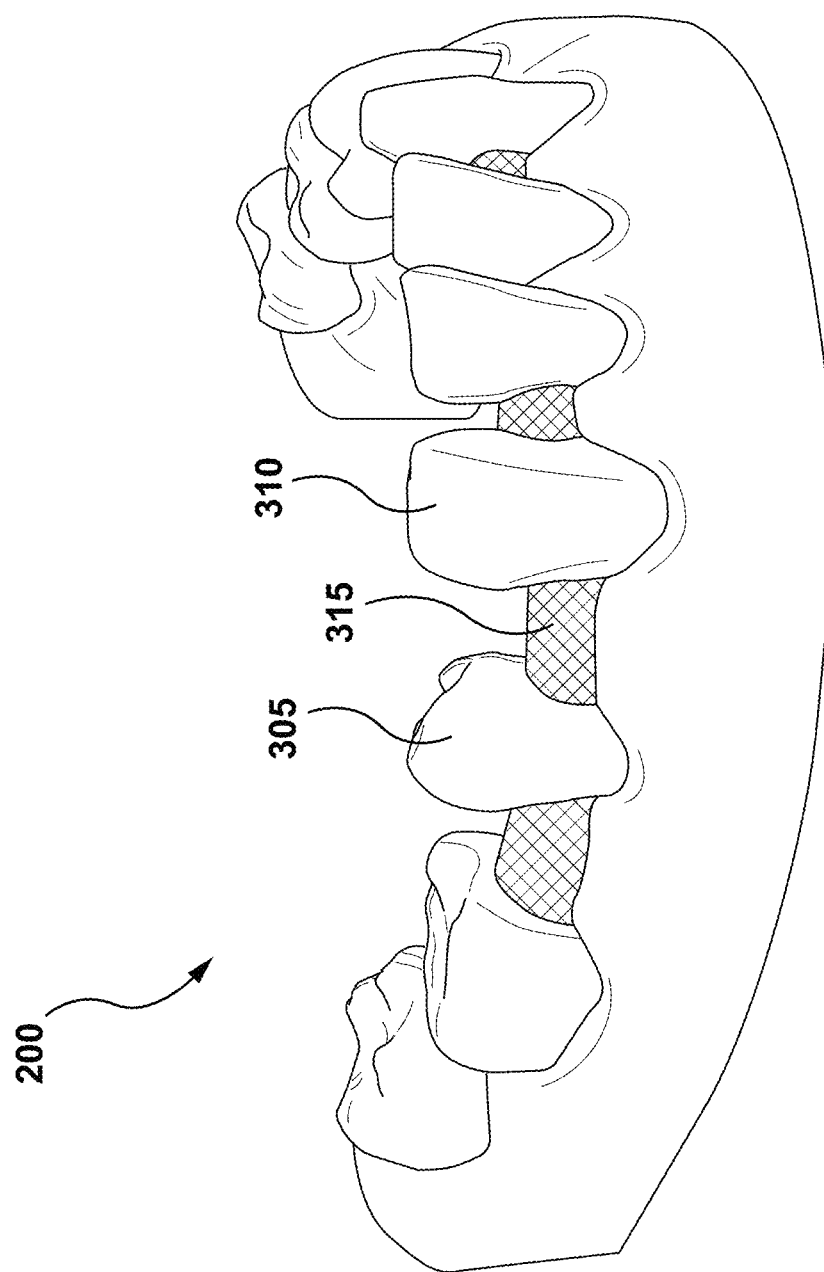
FIG. 3 shows an example of an archform with interdental filler models according to non-limiting embodiments of the present technology.
Figure 4:
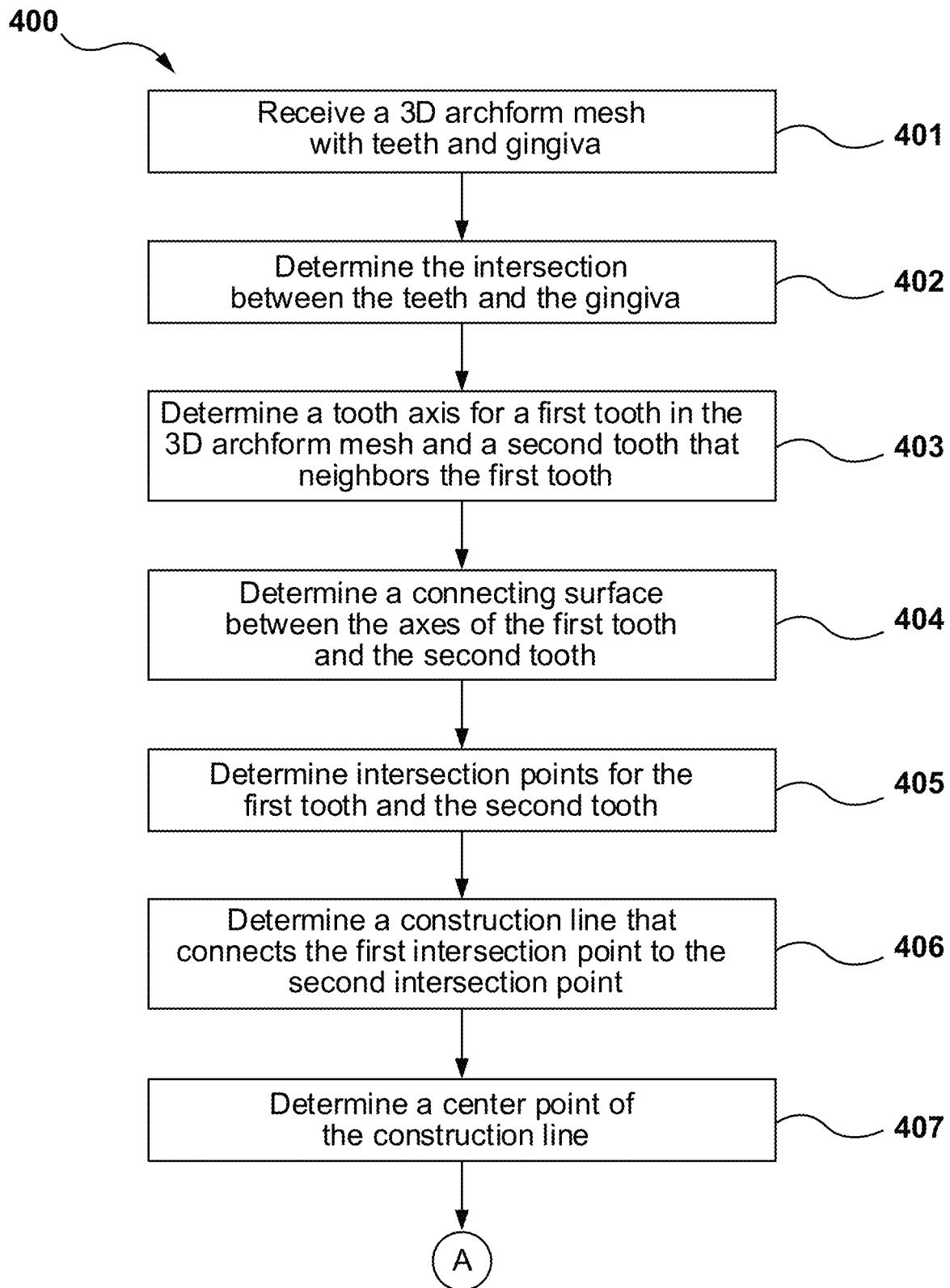
FIGS. 4-7 are flow diagrams of a method for generating an interdental filler model according to non-limiting embodiments of the present technology.
Figure 5:
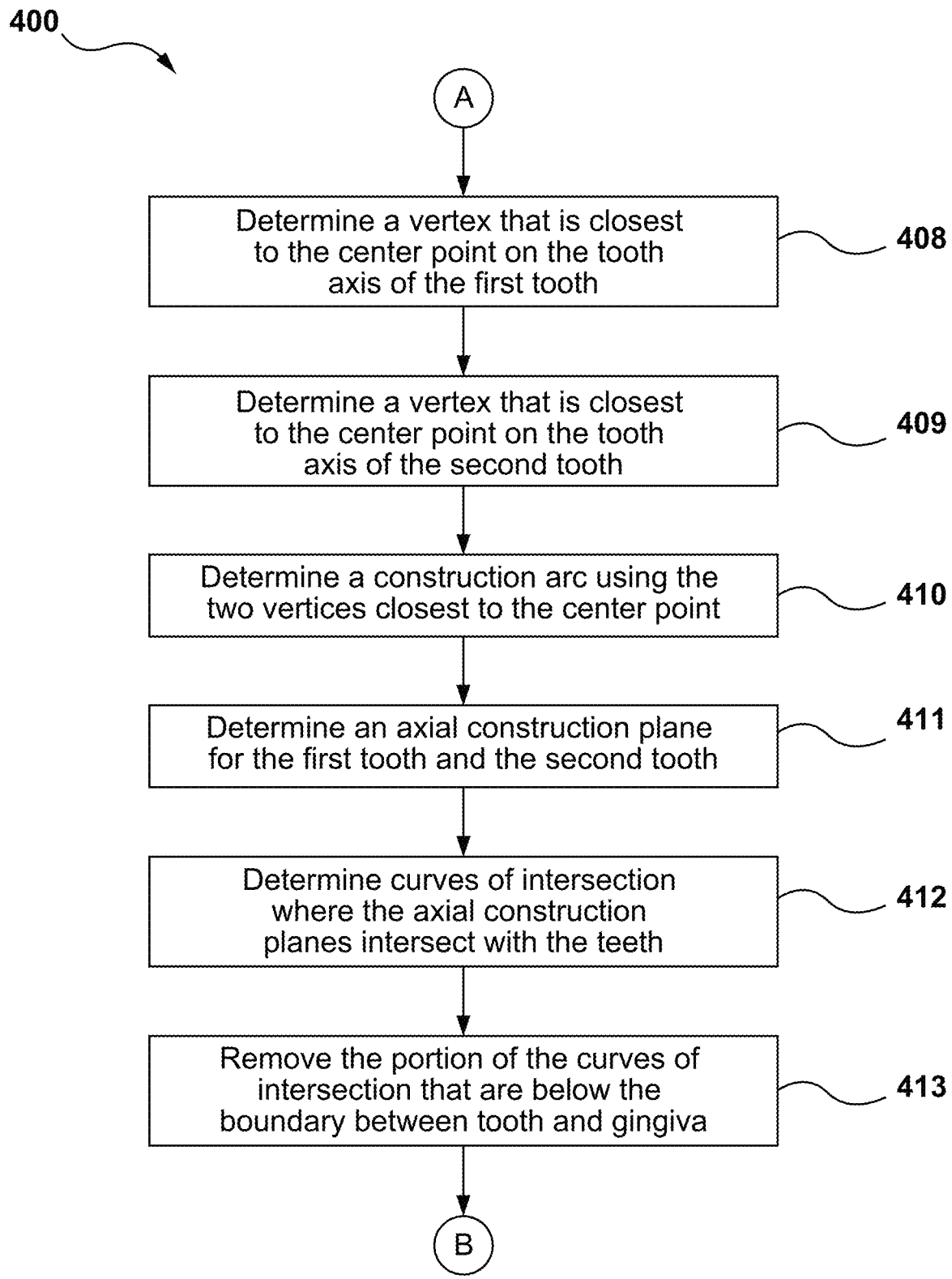
Figure 6:
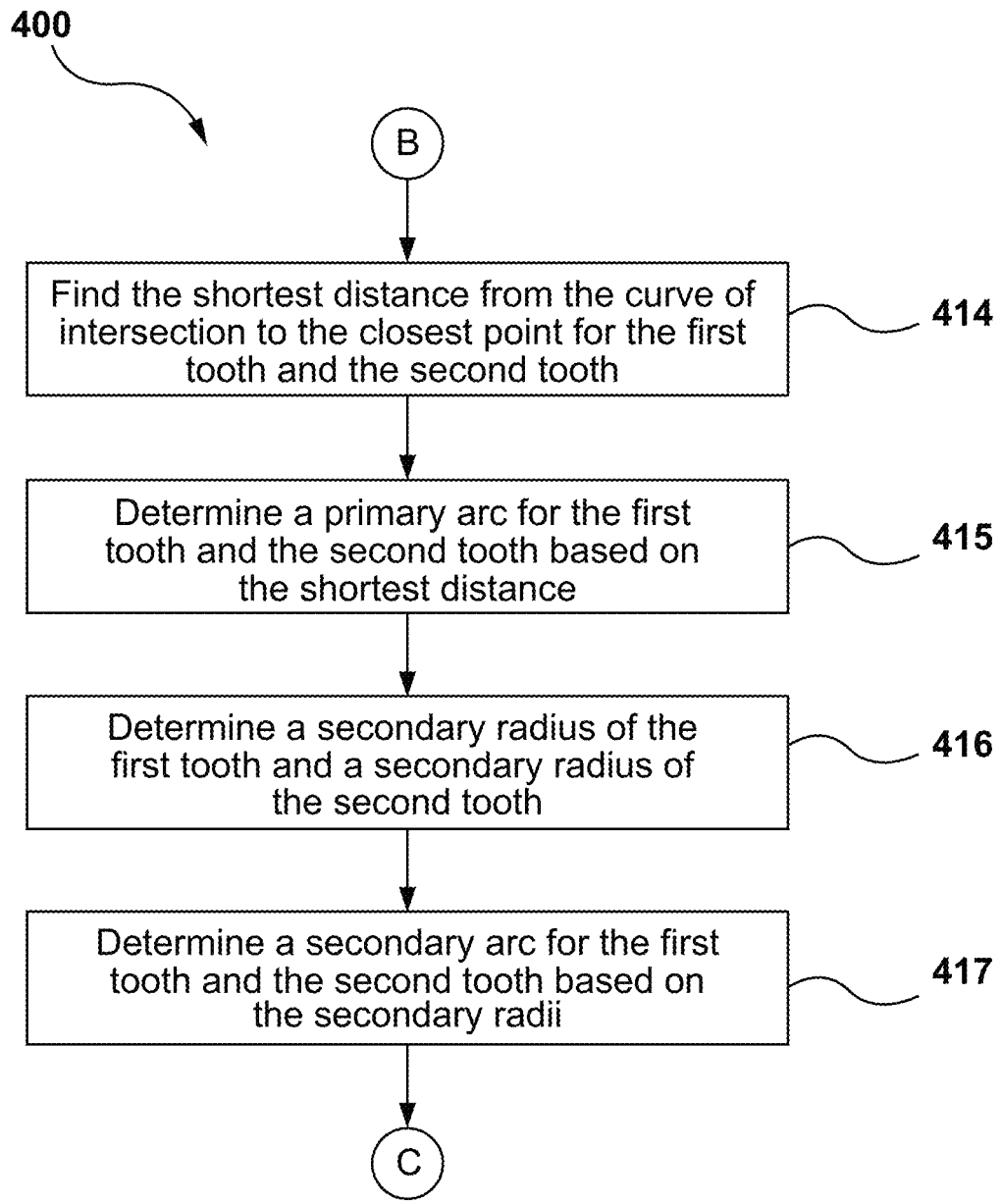
Figure 7:
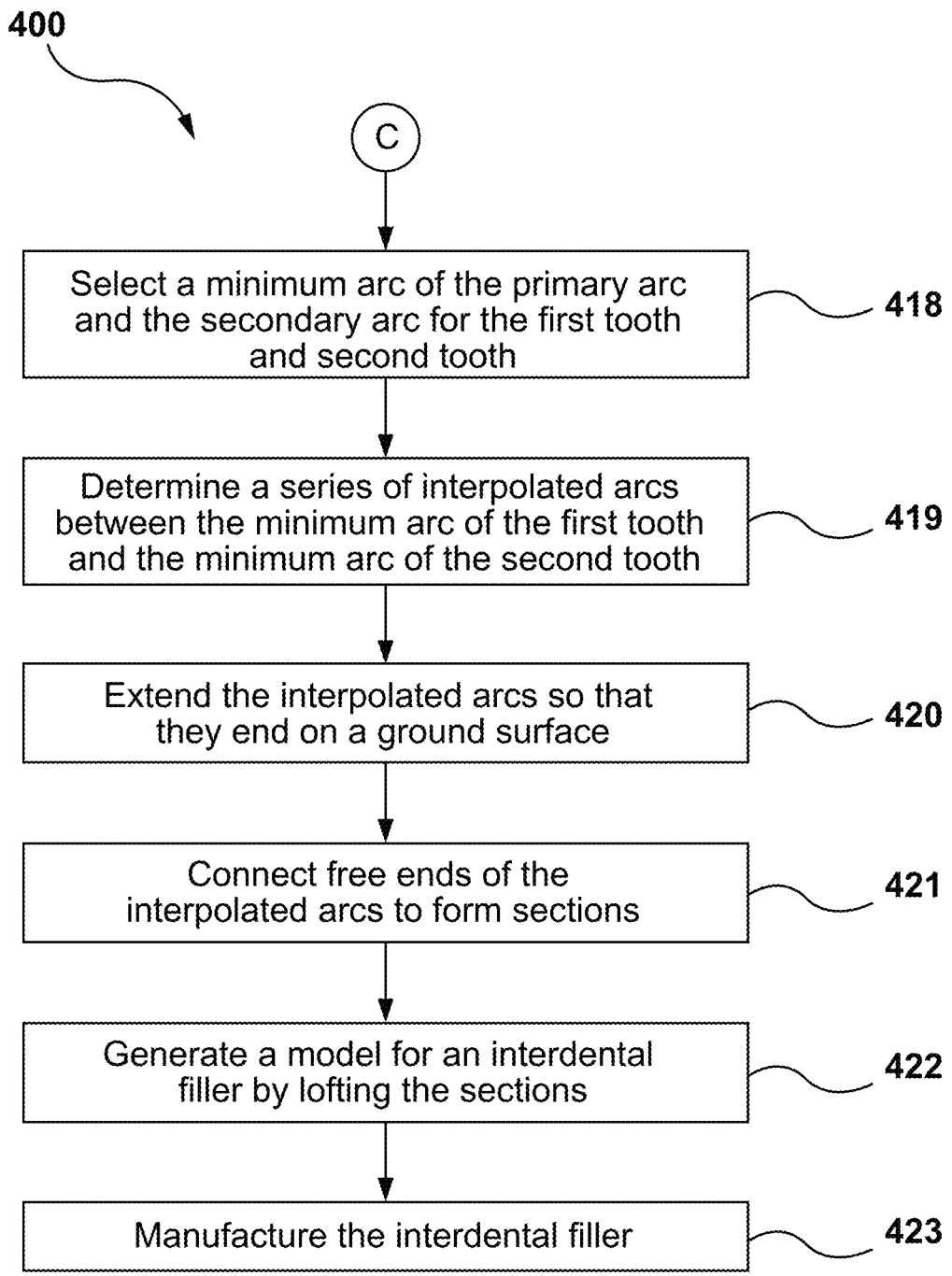

FIG. 3 shows an example schematic diagram of an archform mesh 200 with interdental filler models according to non-limiting embodiments of the present technology. As can be appreciated from FIG. 3, the patient has interdental gaps between several of the teeth 230, including a first tooth 305 and a second tooth 305. An interdental filler model 315 has been generated to fill the interdental gap between the first tooth 305 and the second tooth 310. If the patient were given an orthodontic appliance without an interdental filler to fill the interdental gap between the first tooth 305 and second tooth 305, such as an interdental filler generated based on the interdental filler model 315, the patient may experience some discomfort. Further the orthodontic appliance may be unsupported due to the interdental gap between the first tooth 305 and the second tooth 310, and the orthodontic appliance may bend and/or otherwise deform. In another example, the orthodontic appliance produced without considering the interdental gap may have a respective indent representative thereof coming into contact with the patient's gingiva, within the interdental gap, when worn over the patient's teeth. An interdental filler generated using the interdental filler model 315 may reduce and/or prevent some or all of these issues caused by the interdental gap when using the orthodontic appliance.

Generally speaking, the orthodontic appliance may be configured to exert a respective predetermined force onto at least one of the teeth 230 of the patient causing them to move towards an aligned position, that is, the position associated with normal occlusion between patient's archforms. In various non-limiting embodiments of the present technology, the orthodontic appliance may comprise orthodontic appliances of different types, shapes, sizes and configurations, such as those including, without limitation, aligners, brackets, multi-strand wires, strips, retainers, and plates.

According to certain non-limiting embodiments of the present technology, the orthodontic appliance, such as an aligner, may be made of a polymer, such as a thermoplastic material. In other non-limiting embodiments of the present technology, the orthodontic appliance may be made of poly-vinyl chloride (PVC). In yet other non-limiting embodiments of the present technology, the orthodontic appliance may be made of polyethylene terephthalate glycol (PETG). Other suitable materials can also be used to form the orthodontic appliance.

Further, in certain non-limiting embodiments of the present technology, the archform mesh 200 including the interdental filler model 315 may be used for producing the orthodontic appliance. In some non-limiting embodiments of the present technology, the orthodontic appliance may be manufactured of one of the above-listed materials using 3D printing techniques where the orthodontic appliance is printed out by a 3D printer according to the archform mesh 200 including the interdental filler model 315.

However, in other non-limiting embodiments of the present technology, the orthodontic appliance may be produced by a thermoforming process where (1) an unfinished orthodontic appliance is produced, using a pre-designed preform, on a respective mold (not depicted) produced based on the archform mesh 200 including the interdental filler model 315; and (2) the unfinished orthodontic appliance is cut to remove excess material therefrom, thereby producing the orthodontic appliance.

How the interdental filler model 315 may be generated by the processor 110, in accordance with certain non-limiting embodiments of the present technology, will be described below with reference to FIGS. 4 to 24, FIGS. 4-7 are flow diagrams of a method 400 for generating an interdental filler model according to non-limiting embodiments of the present technology. In one or more aspects, the method 400 or one or more steps thereof may be performed by a processor, such as the processor 110 of the computer system 100. The method 400 or one or more steps thereof may be embodied in computer-executable instructions that are stored in a computer-readable medium, such as a non-transitory mass storage device, loaded into memory and executed by a CPU. Some steps or portions of steps in the flow diagram may be omitted or changed in order.

For ease of explanation, the method 400 and following figures describe the generation of a single interdental filler model for filling an interdental gap between two teeth. It should be understood that any number of interdental filler models may be generated for a patient depending on a respective number of interdental gaps within the teeth 230. For example, the archform mesh 200 may include several interdental filler models. Interdental filler models may be generated for each interdental gap in the patient's archform. The user may select the number of interdental filler models to generate. For example, the user may select two neighboring teeth on a user interface and request that an interdental filler model be generated for an interdental gap between the two selected teeth.

Step 401: Receive a 3D Archform Mesh

At step 401, according to certain non-limiting embodiments of the present technology, the processor 110 may be configured to receive a 3D archform mesh, such as the archform mesh 200. As mentioned above, the archform mesh 200 may represent the patient's mouth. The archform mesh 200 may comprise the teeth 230 and the gingiva 220.

In some non-limiting embodiments of the present technology, the archform mesh 200 may be received as a set of vertices and/or edges connecting the vertices. The archform mesh 200 may be received in any suitable format. As described above, the archform mesh 200 may have been generated based on scans, images, a mold of the patient's mouth, and/or any other data related to the patient. The archform mesh 200 may include at least one interdental gap between two teeth in the 3D archform mesh, such as the interdental gap between the first tooth 305 and the second tooth 305.

Step 402: Determine the Intersection Between the Teeth and the Gingiva

At step 402, according to certain non-limiting embodiments of the present technology, intersection lines between the teeth 230 and the gingiva 220 may be determined. The intersection lines may trace the boundary 210 separating the teeth 230 from the gingiva 220. The intersection lines may be determined automatically and/or drawn by a user. In specific non-limiting embodiments of the present technology, the processor 110 may be configured to determine the intersection lines using one of the methods described in the co-owned U.S. Pat. No. 10,695,147-B1. More specifically, according to certain non-limiting embodiments of the present technology, in order to determine the boundary 210, the processor 110 may be configured to: (i) receive the archform mesh 200; (ii) define, for each tooth of the teeth 230 of the archform mesh 200, a plurality of curves, wherein each curve of the plurality of curves crosses the boundary 210 between the teeth 230 and the gingiva 220; determine, for each point of a plurality of points of each of the plurality of curves, an indication of curvature of the respective curve at each point; determine, for each point of the plurality of points and based on the indication of curvature corresponding to the respective point, a predicted likelihood parameter that each point corresponds to the boundary 210 between the teeth 230 and the gingiva 220; and select, for each curve of the plurality of curves, using a smoothing function and the predicted likelihood parameter, a single point, of the plurality of points, on the respective curve as a boundary point corresponding to the boundary 210 between the teeth 230 and the gingiva 220 of the archform mesh 200.

Figure 8:
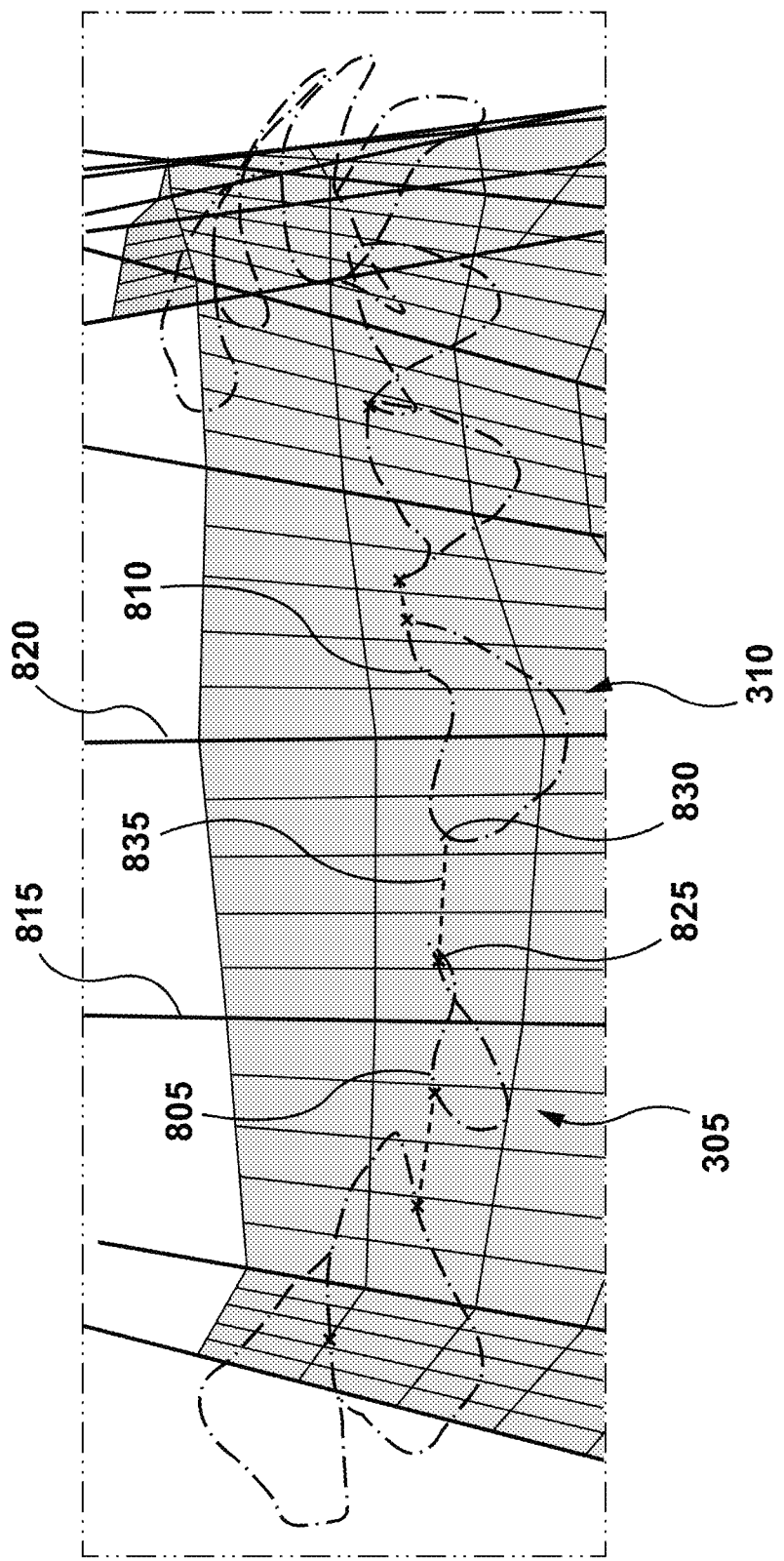
FIG. 8 shows an example of an archform with construction lines according to non-limiting embodiments of the present technology.

An intersection line may be determined for each tooth. The intersection lines for multiple teeth may intersect, such as when the teeth are neighboring teeth and there is not an interdental gap between the neighboring teeth. A first intersection line may be determined for the first tooth 305 and a second intersection line may be determined for the second tooth 305. FIG. 8, described below, illustrates an example of the first intersection line for the first tooth 305 and the second intersection line for the second tooth 305.

The intersection lines may be shifted vertically based on a predetermined aligner edge offset value. The aligner edge offset value may be the distance of the end of the cut of an orthodontic appliance, such as an aligner, relative to the surface of the gingiva. For example, the predetermined aligner edge offset value may be 0.4 mm. However, in other non-limiting embodiments of the present technology, predetermined aligner edge offset value may be 0.2 mm, 0.5 mm, or even 1 mm. The predetermined aligner edge offset value may be adjusted by the user of the computer system 100, such as an operator designing the orthodontic appliance.

Step 403: Determine Tooth Axes

At step 403, in some non-limiting embodiments of the present technology, the processor 110 may be configured to determine a respective tooth axis for some or all of the teeth 230 in the archform mesh 200. For example, the processor 110 may be configured to determine respective tooth axes for each of the teeth 230 or for a subset thereof in the archform mesh 200. It is not limited how the processor 110 may be configured to determine a given tooth axis; however, in specific non-limiting embodiments of the present technology, the processor 110 may be configured to apply one of methods and/or systems described in a co-owned U.S. Pat. No. 10,856,954-B1 issued on Dec. 8, 2020, entitled "SYSTEMS AND METHODS FOR DETERMINING TOOTH CENTER OF RESISTANCE" which is incorporated herein by reference.

More specifically, to determine a first tooth axis, for example, for the first tooth 305, the processor 110 may be configured to: (1) receive image data of a crown portion of the first tooth 305; (2) identify an internal reference point in the image data, the internal reference point being based on a predetermined internal reference point instruction for locating the internal reference point in a given tooth crown by: obtaining a mesial point on a mesial side of the crown portion, and a distal point on a distal side of the crown portion; generating a mesiodistal line joining the mesial point and the distal point; identifying the mesiodistal center as a midpoint on the mesiodistal line; (3) determine a reference plane in the image data, the reference plane being perpendicular to the mesiodistal line and extending through the mesiodistal center; (4) determine an intersection curve based on an intersection of the reference plane and the crown portion, the intersection curve following a shape of the surface of the crown portion at the reference plane; and (5) determine the first tooth axis of the first tooth 305 based on the intersection curve.

In order to generate the interdental filler model 315 for the interdental gap between the first tooth 305 and the second tooth 305, the processor 110 may be configured to determine the first tooth axis for the first tooth 305 and a second tooth axis for the second tooth 305. FIG. 8, described below, illustrates tooth axes for the first tooth 305 and the second tooth 310. The tooth axes may be adjusted by the user. For example, the user may select a tooth axis on a user interface and adjust the position and/or angle of the tooth axis.

Step 404: Determine a Connecting Surface

At step 404, the processor 110 may be configured to determine a connecting surface between the first tooth axis of the first tooth 305 and the second tooth axis of the second tooth 310. Further, for each tooth axis, the processor 110 may be configured to determine two corners of the connecting surface. The corners for the first tooth 305 may be determined by projecting the highest and lowest vertices of the mesh of the first tooth 305 on the tooth axis of the first tooth 305. Similarly, the corners for the second tooth 305 may be determined by projecting the highest and lowest vertices of the second tooth 305 on the tooth axis of the second tooth 305. The four vertices, two on the tooth axis of the first tooth 305 and two on the tooth axis of the second tooth 305, may then be connected to form the connecting surface between the first tooth 305 and the second tooth 310.

Step 405: Determine Intersection Points

At step 405, in some non-limiting embodiments of the present technology, the processor 110 may be configured to determine a first intersection point on the first tooth 305 and a second intersection point on the second tooth 305. FIG. 8, described below, illustrates intersection points determined for the first tooth 305 and the second tooth 310.

The intersection points may be vertices that are located on the intersection lines determined at step 402 and the connecting surface determined at step 404. In other words, the intersection points may be the intersection of the connecting surface and the two intersection lines. An intersection point for the first tooth 305 may be a vertex where the connecting surface and the intersection line of the first tooth 305 intersect. An intersection point for the second tooth 305 may be a vertex where the connecting surface and the intersection line of the second tooth 305 intersect.

Various other methods may be used for determining the intersection points. For example, they may be manually selected by a user. In another example, two points on the intersection lines of the first tooth 305 and the second tooth 305 that are the closest to each other may be selected as the intersection points. The intersection points may define ends of the interdental filler model 315.

Step 406: Determine a Construction Line

At step 406, according to certain non-limiting embodiments of the present technology, the processor 110 may be configured to determine a construction line that connects the first intersection point of the first tooth 305 to the second intersection point of the second tooth 305. FIG. 8, described below, illustrates construction lines connecting intersection points. The construction line may be a straight line connecting the intersection points determined at step 405. The construction line may extend from the first tooth 305 to the second tooth 305. The construction line may extend across the interdental gap between the first tooth 305 and the second tooth 305.

Step 407: Determine a Center Point of the Construction Line

At step 407, according to certain non-limiting embodiments of the present technology, the processor 110 may be configured to determine a center point of the construction line. The center point may be a vertex that is equidistant from the first intersection point on the first tooth 305 and the second intersection point on the second tooth 305. The center point may be found without determining the construction line, in which case step 406 may be skipped. To find the center point without determining the construction line, a vertex that is equidistant from the two intersection points may be selected, where the selected vertex minimizes the distance from the selected vertex to the intersection points.

Steps 408 and 409: Determine a Closest Vertex on the Tooth Axes

Figure 10:
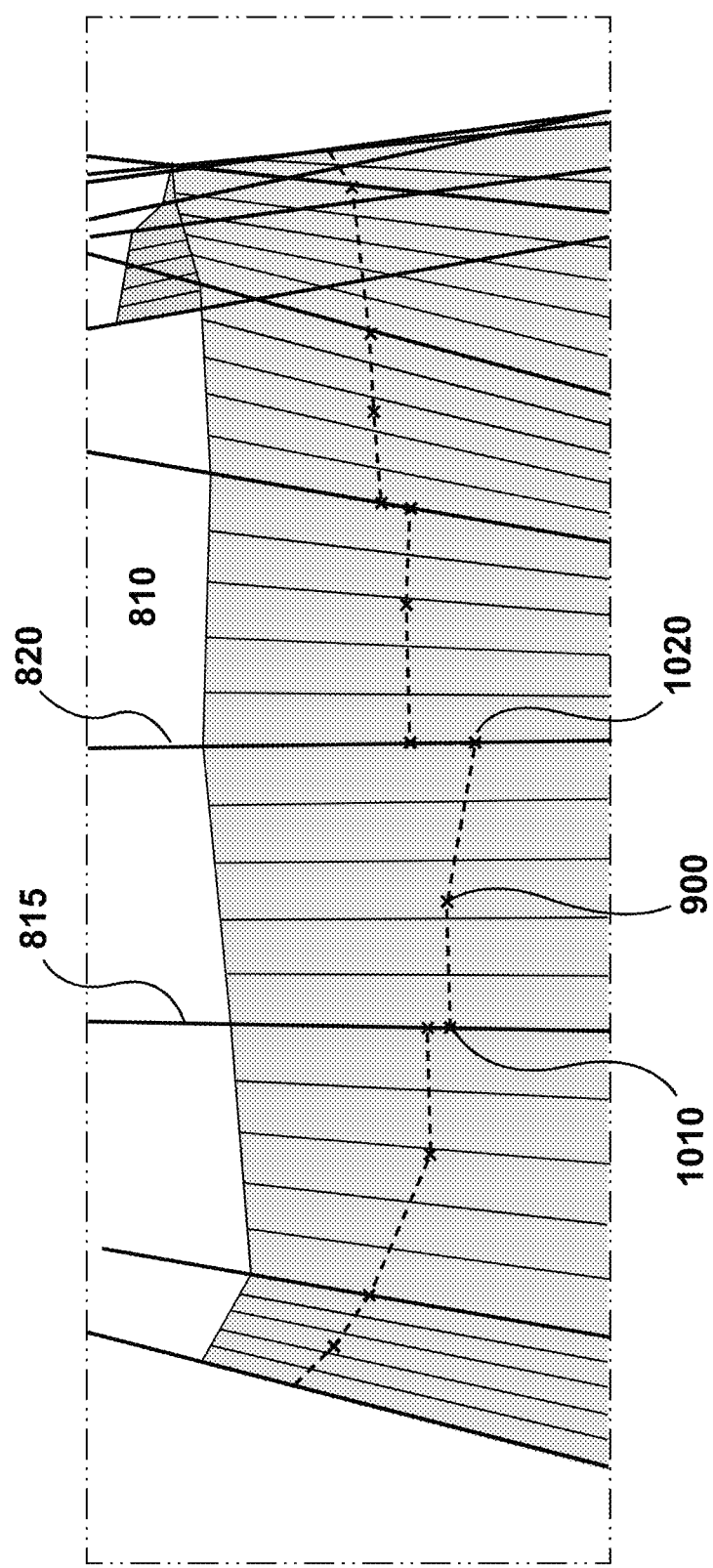
FIG. 10 shows an example of closest vertices according to non-limiting embodiments of the present technology

At step 408, according to certain non-limiting embodiments of the present technology, the processor 110 may be configured to determine a first closest vertex on the first tooth axis of the first tooth 305 that is closest to the center point. Similarly, at step 409, the processor 110 may be configured to determine a second closest vertex on the second tooth axis of the second tooth 305 that is closest to the center point. FIG. 10, described below, illustrates the first and second closest vertices on the respective teeth axes of the first tooth 305 and the second tooth 310.

Step 410: Determine a Construction Arc

Figure 11:
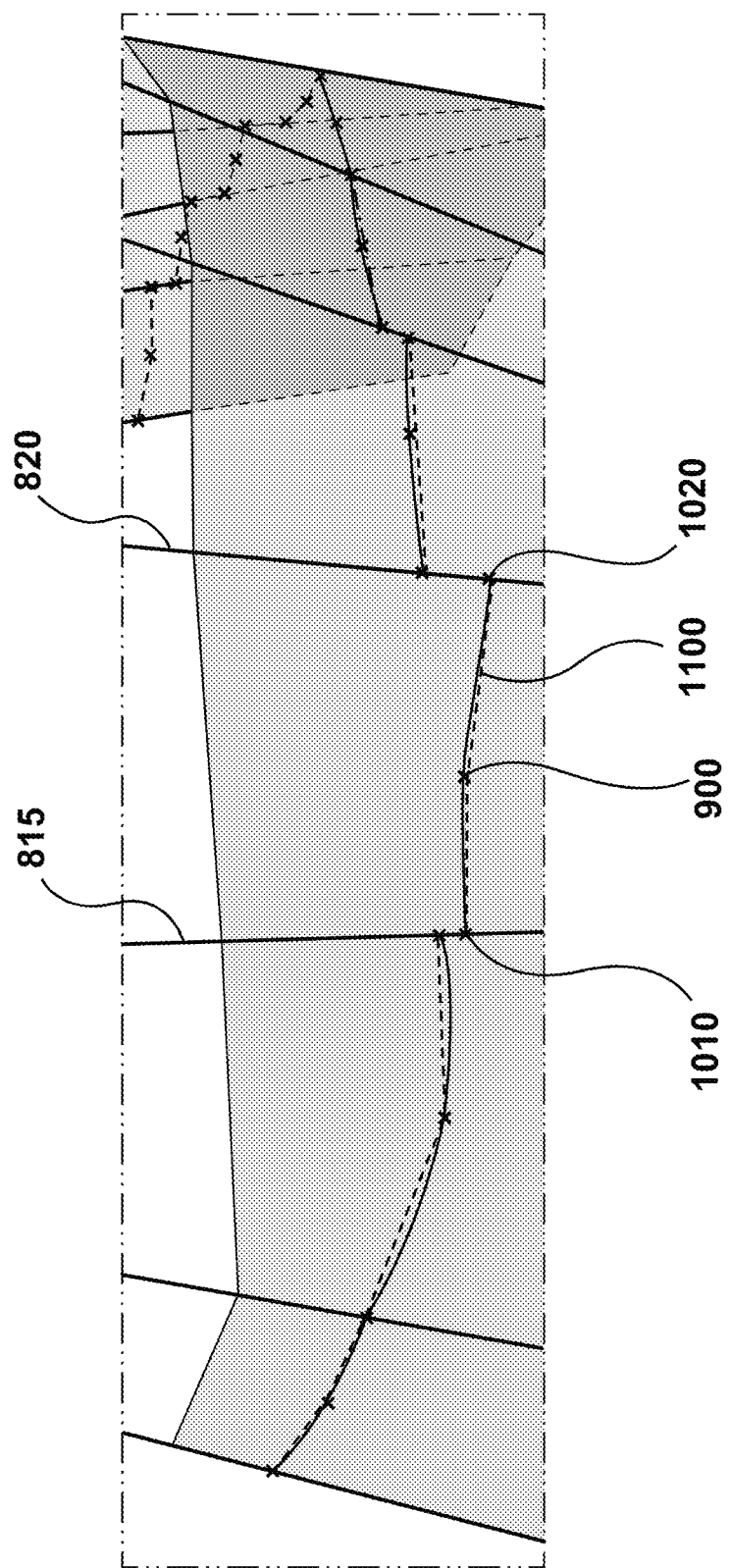
FIG. 11 shows an example of construction arcs according to non-limiting embodiments of the present technology.

At step 410, the processor 110 may be configured to determine a construction arc. According to certain non-limiting embodiments of the present technology, the construction arc may define a curvature of the interdental filler model 315 filling the interdental gap between the first tooth 305 and the second tooth 310. The processor 110 may be configured to determine the construction arc based on the closest vertices determined at steps 408 and 409 and the center point determined at step 407. The construction arc may be a three-point arc connecting the first vertex on the first tooth axis of the first tooth 305, the center point, and the second vertex on the second tooth axis of the second tooth 305. FIG. 11, described below, illustrates examples of construction arcs.

A user may manually select and/or adjust the construction arc. For example, the user may reposition the center point of a construction arc. After the user has repositioned the center point, the construction arc may be determined again using the repositioned center point.

Figure 12:
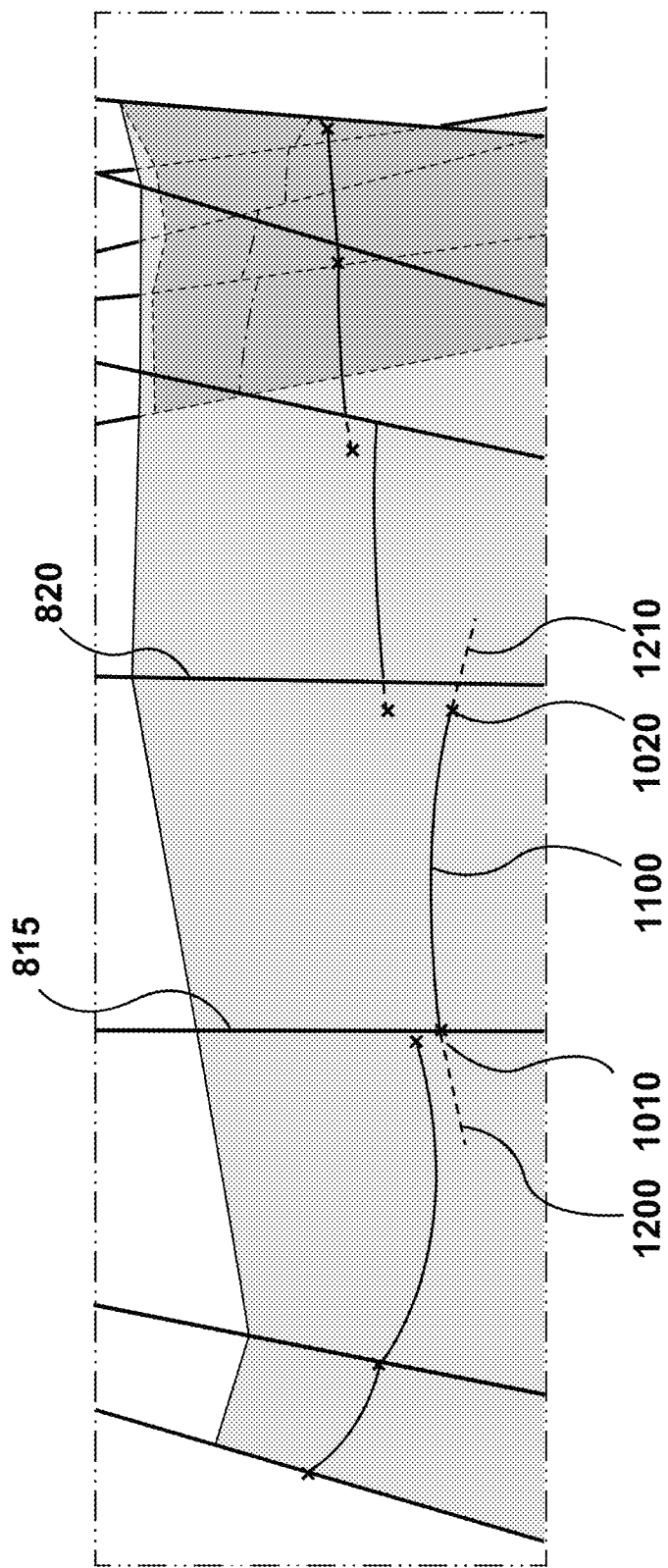
FIG. 12 shows an example of construction arc tangent vectors according to non-limiting embodiments of the present technology.

Arc tangent vectors may be determined at either end of the construction arcs. FIG. 12, described below, illustrates an example of arc tangent vectors. The arc tangent vectors may be used to determine axial construction planes.

Step 411: Determine Construction Planes

Figure 13:
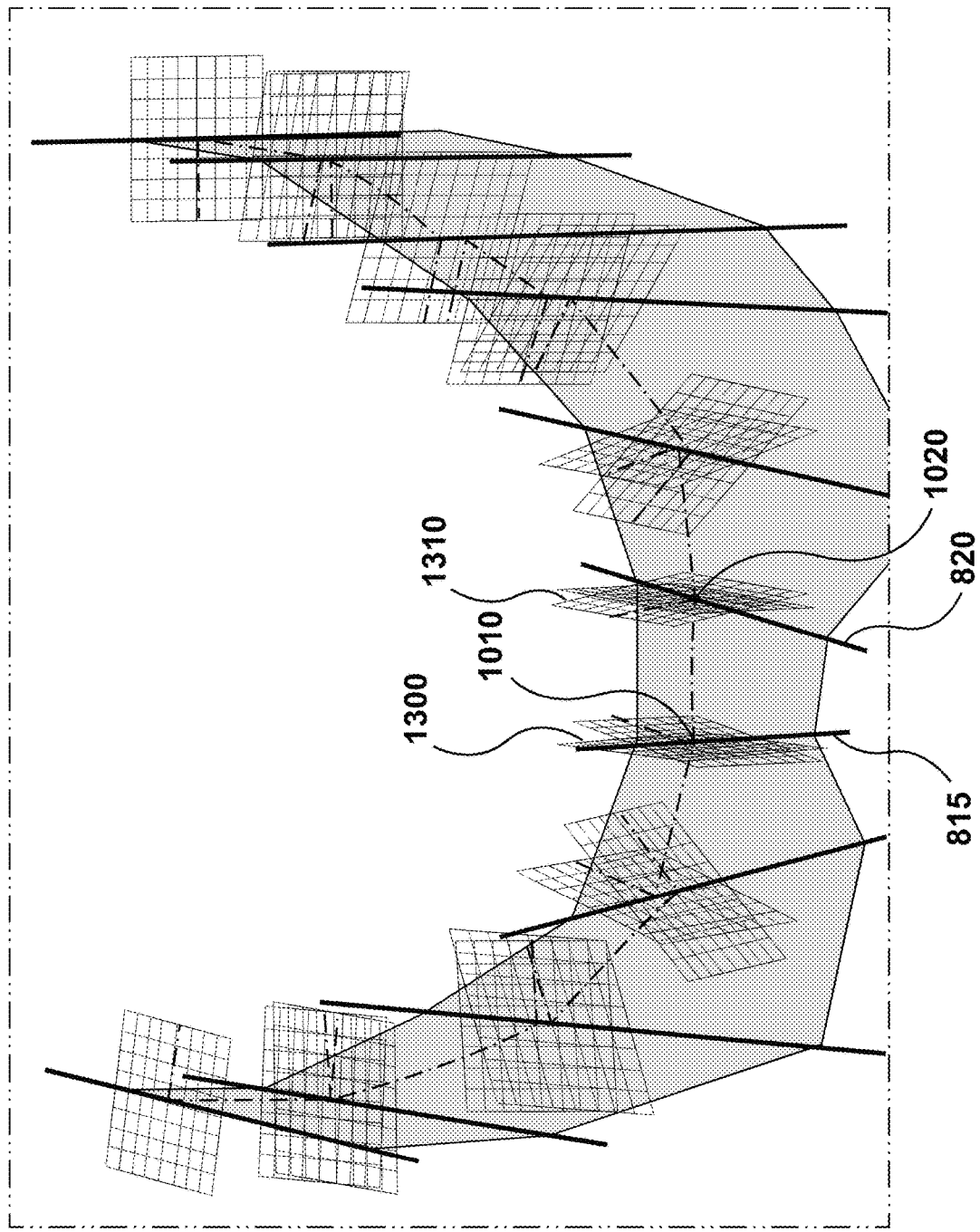
FIG. 13 shows an example of axial construction planes according to non-limiting embodiments of the present technology.

At step 411, according to certain non-limiting embodiments of the present technology, the processor 110 may be configured to determine axial construction planes. A first axial construction plane may be determined for the first tooth 305 and a second axial construction plane may be determined for the second tooth 305. FIG. 13, described below, illustrates axial construction planes.

The axial construction planes may include the closest vertices determined at steps 408 and 409. The respective closest vertices may form the center of each the construction planes. The first closest vertex on the first tooth axis of the first tooth 305 may be the center of the construction plane generated for the first tooth 305. The y-axis of the construction plane generated for the first tooth 305 may be the first tooth axis of the first tooth 305. The x-axis of the construction plane generated for the first tooth 305 may be the cross product of the arc tangent vector at the first tooth 305 and the second tooth axis of the second tooth 305. Similarly, the y-axis of the construction plane for the second tooth 305 may be the second tooth axis of the second tooth 305, and the x-axis may be the cross product of the arc tangent vector at the second tooth 305 and the tooth axis of the second tooth 305.

Step 412: Determine Curves of Intersection

Figure 14:
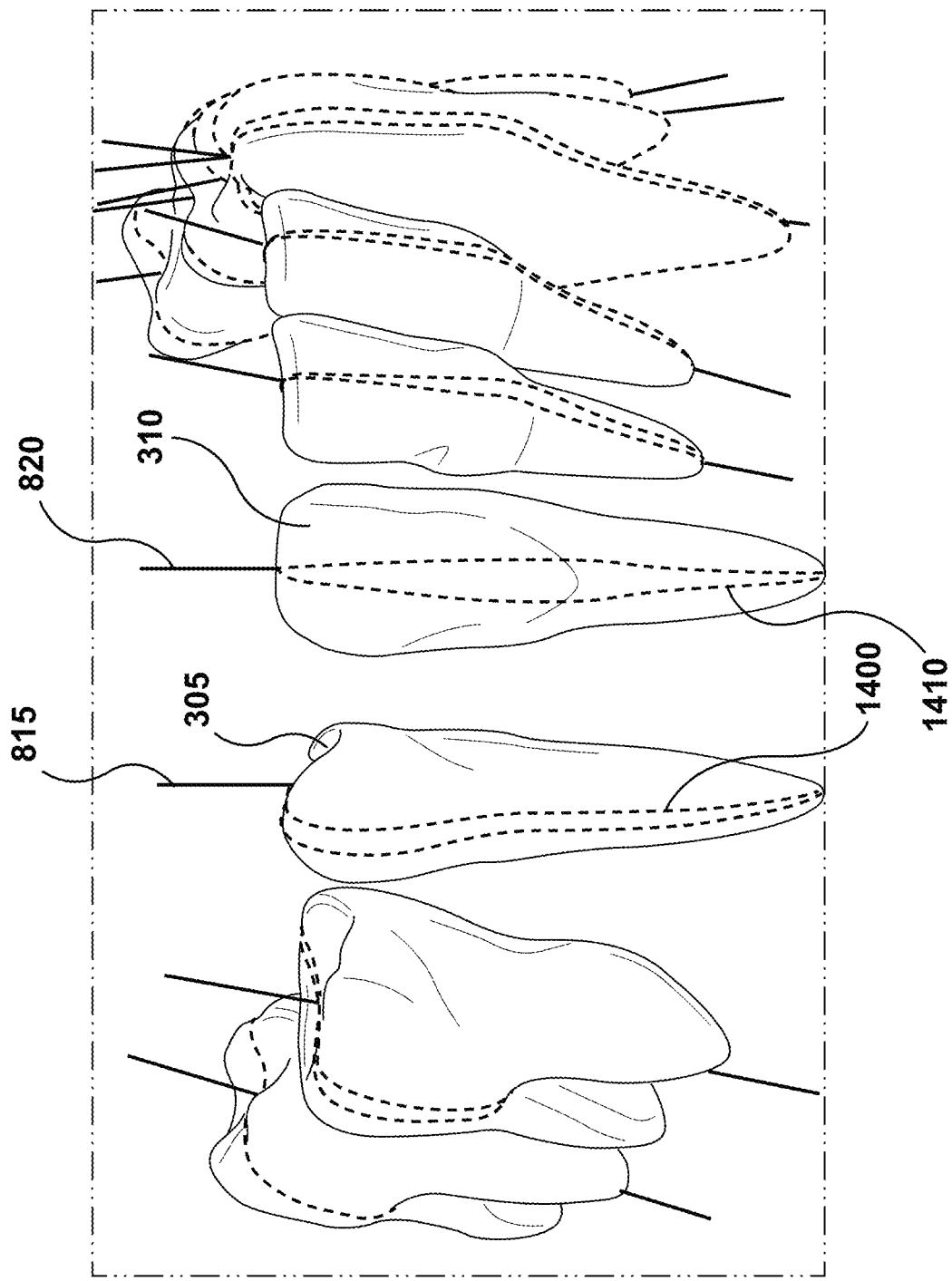
FIG. 14 shows an example of curves of intersection according to non-limiting embodiments of the present technology.

At step 412, according to certain non-limiting embodiments of the present technology, the processor 110 may be configured to determine curves of intersection for the first tooth 305 and the second tooth 305. A first curve of intersection for the first tooth 305 may be the intersection of the axial construction plane for the first tooth 305 and the tooth mesh of the first tooth 305. Similarly, a second curve of intersection for the second tooth 305 may be the intersection of the axial construction plane for the second tooth 305 and the tooth mesh of the second tooth 305. FIG. 14, described below, illustrates curves of intersection.

Step 413: Remove Portions of the Curves of Intersection

Figure 15:
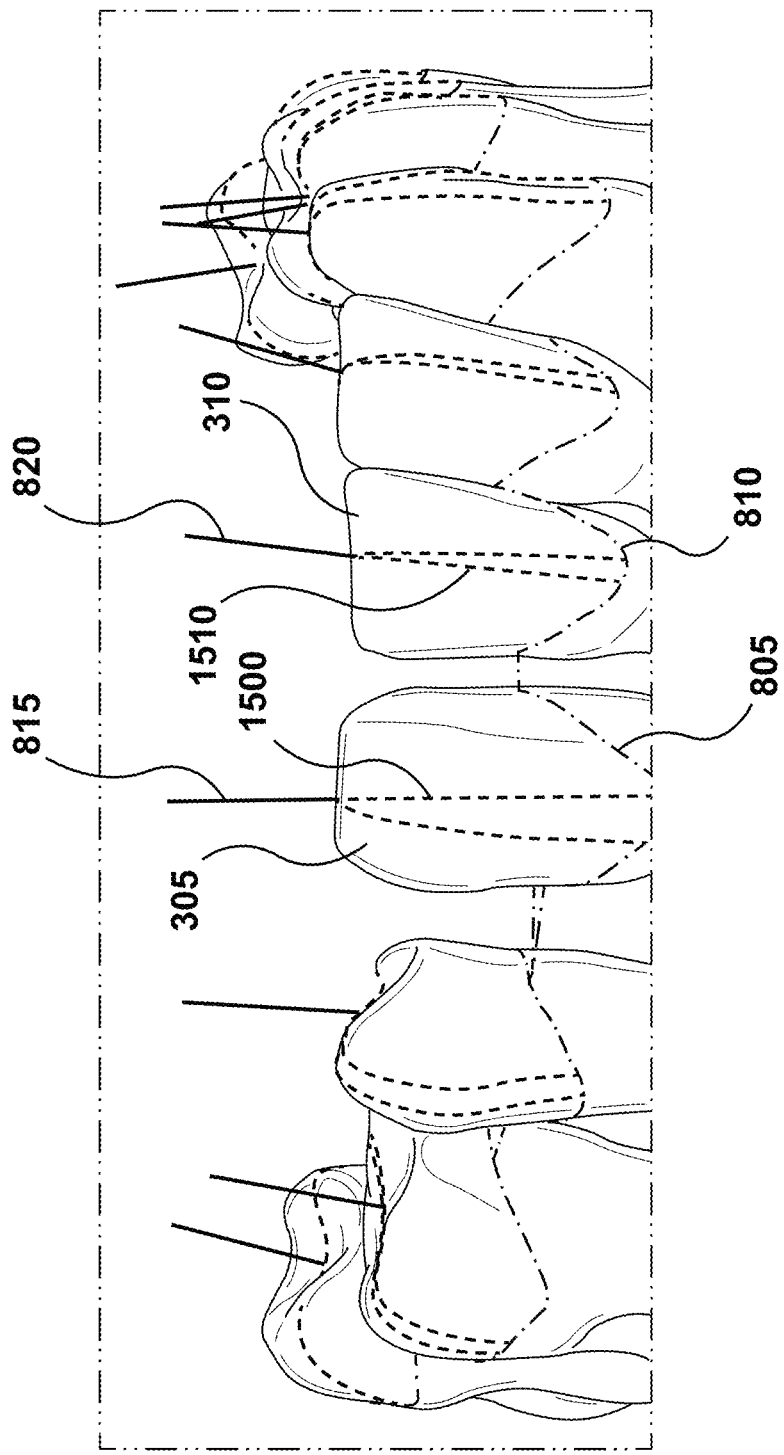
FIG. 15 shows an example of portions of the curves of intersection according to non-limiting embodiments of the present technology.

At step 413, according to certain non-limiting embodiments of the present technology, the processor 110 may be configured to remove portions of the curves of intersection determined at step 412. Portions that are below the intersection between the teeth 230 and gingiva 220 determined at step 402 may be removed from the curves of intersection. FIG. 15, described below, illustrates curves of intersection after the portions below the intersection between the teeth and gingiva have been removed.

Figure 16:
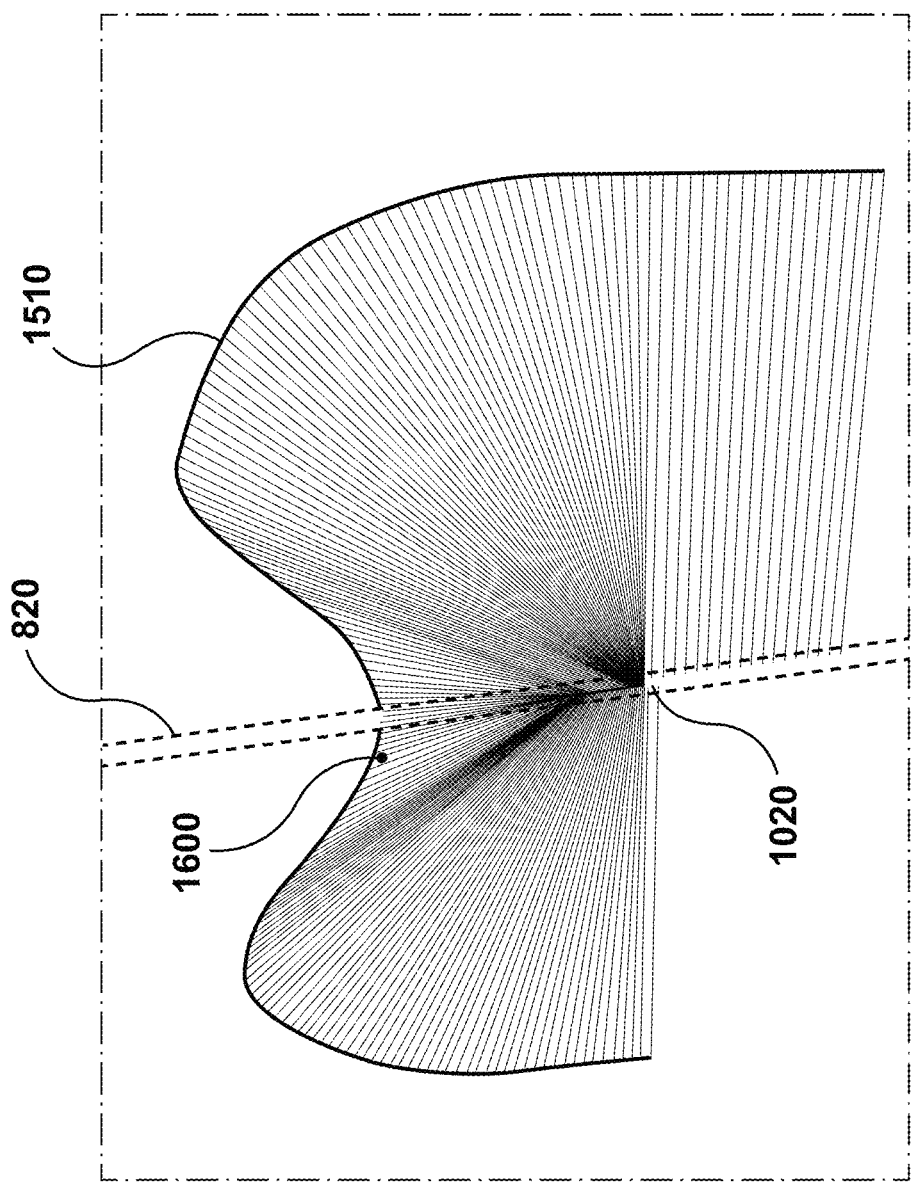
FIG. 16 shows an example of distances on a curve of intersection according to non-limiting embodiments of the present technology.

Step 414: Find the Shortest Distance from the Curve of Intersection to the Closest Vertex At step 414, according to certain non-limiting embodiments of the present technology, the processor 110 may be configured to determine a shortest distance from the portions of the curves of intersection determined at step 413 to the closest vertex on each tooth determined at steps 408 and 409. FIG. 16, described below, illustrates distances between points on the curve of intersection for a tooth and the closest vertex on the tooth.

For example, the processor 110 may be configured to determine a minimum distance between a point on the curve of intersection for the first tooth 305 and the first closest vertex on the first tooth 305. Similarly, the processor 110 may be configured to determine a minimum distance between a point on the curve of intersection for the second tooth 305 and the second closest vertex on the second tooth 305.

Step 415: Determine Primary Arcs

Figure 17:
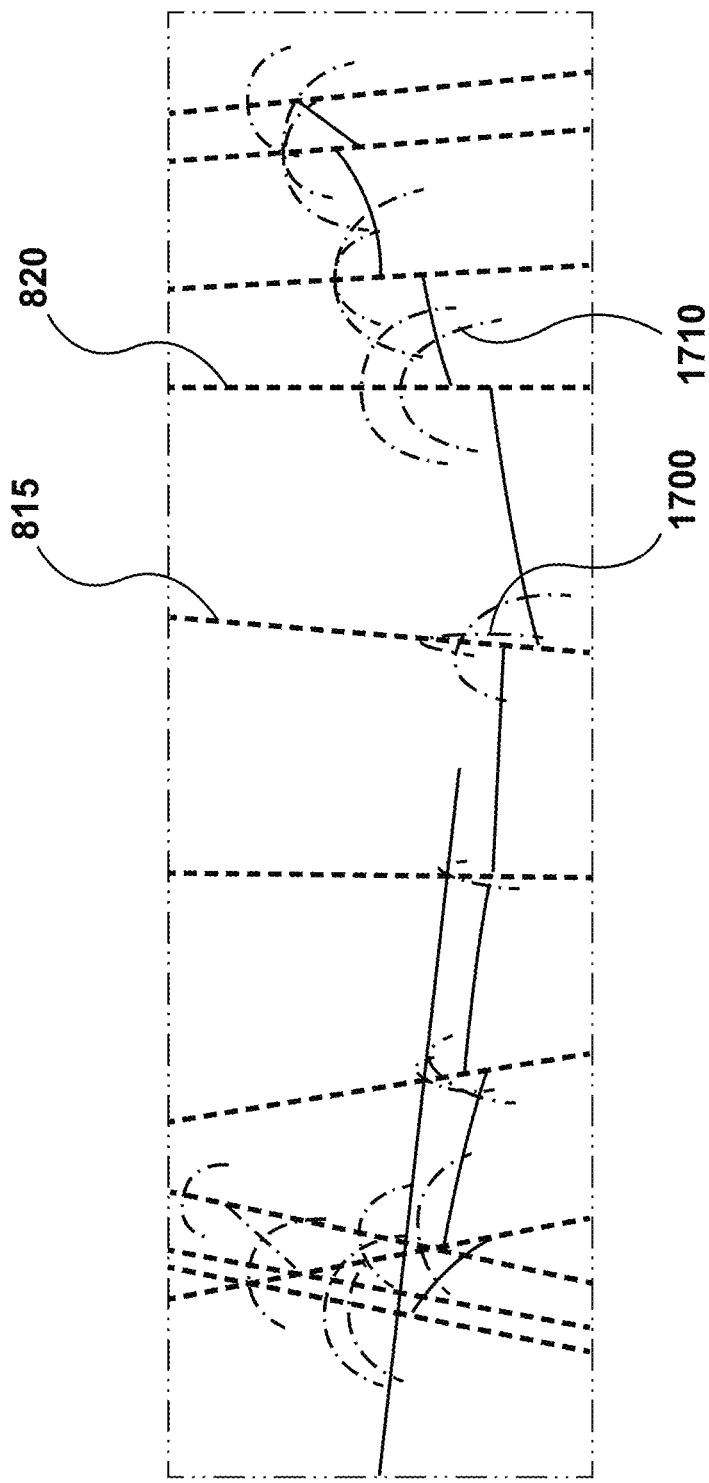
FIG. 17 shows an example of primary arcs according to non-limiting embodiments of the present technology.

At step 415, according to certain non-limiting embodiments of the present technology, the processor 110 may be configured to determine primary arcs for the first tooth 305 and the second tooth 305. FIG. 17, described below, illustrates primary arcs. A center of a first primary arc for the first tooth 305 may be in the axial construction plane of the first tooth 305. Similarly, a center of a second primary arc for the second tooth 305 may be in the axial construction plane of the second tooth 305.

The radius of the construction arc for a tooth may be determined based on a respective shortest distance determined at step 414 for the respective tooth. A predetermined distance may be subtracted from the shortest distance to determine the radius. For example, 0.2 mm may be subtracted from the shortest distance. However, in other non-limiting embodiments of the present technology, the predetermined distance may be 0.1 mm, 0.3 mm, or 0.7 mm, as an example.

Step 416: Determine a Secondary Radius

Figure 18:
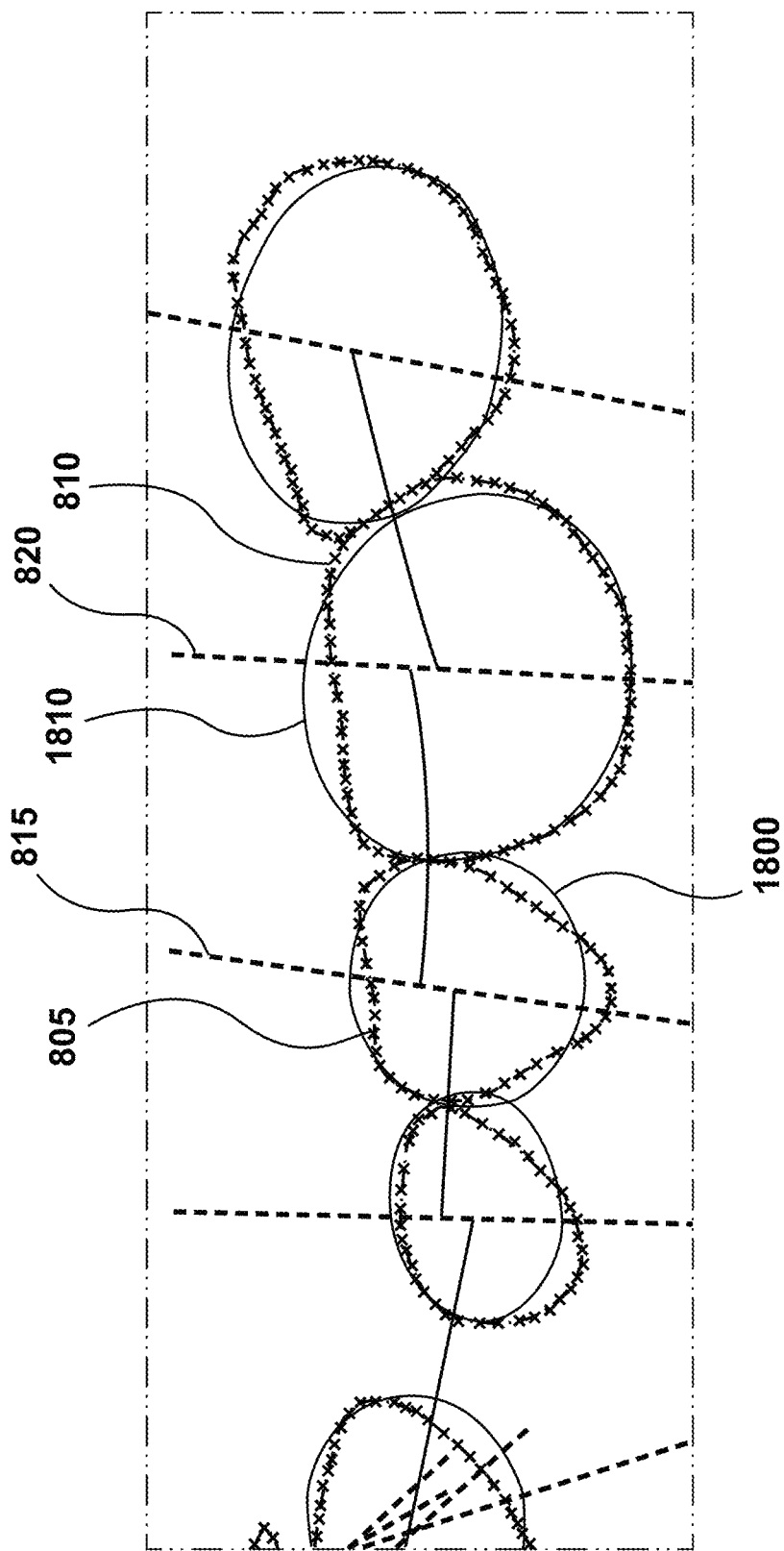
FIG. 18 shows an example of points used to determine a secondary radius according to non-limiting embodiments of the present technology.

At step 416, according to certain non-limiting embodiments of the present technology, the processor 110 may be configured to determine secondary radii for the first tooth 305 and the second tooth 305. To determine a first secondary radius for the first tooth 305, the processor 110 may be configured to determine a set of equally distributed points on the intersection line corresponding to the first tooth 305. FIG. 18, described below, illustrates sets of equally distributed points that may be used to determine the secondary radii.

Any number of points may be used in the set of equally distributed points. An arithmetic average of the distributed points may be determined. The arithmetic average may be used as a center of a circle generated for the first tooth 305.

Further, the processor 110 may be configured to use a best fitting plane function to determine a plane corresponding to the first tooth 305. Each of the points in the set of equally distributed points may be input to the best fitting plane function, and the best fitting plane function may determine a plane corresponding to the set of equally distributed points. Each point of the set of equally distributed points may be projected on this plane. A distance between each of the projected points and the center of the circle may be determined. The average of all of the distances may be determined. This average may be used as a radius for calculating secondary arcs, and is referred to herein as a secondary radius. A secondary radius may be determined for the second tooth 305 using the same steps described above with regard to the first tooth 305.

Step 417: Determine Secondary Arcs

At step 417, according to certain non-limiting embodiments of the present technology, the processor 110 may be configured to determine secondary arcs for the first tooth 305 and the second tooth 305. The secondary arcs may be generated similarly to the primary arcs determined at step 415, except the radius of the secondary arcs may be determined based on the secondary radius for the respective tooth. The radius of the secondary arc may be determined by dividing the secondary radius by a predetermined number. For example, the secondary radius of the first tooth 305 may be divided by two to determine the radius of the secondary arc for the first tooth 305. However, other divisor values can also be envisioned, such as 3 or 4, as an example, without departing from the scope of the present technology.

Step 418: Select a Minimum Arc for Each Tooth

At step 418, according to certain non-limiting embodiments of the present technology, the processor 110 may be configured to select the primary arc or secondary arc for each one of the first tooth 305 and the second tooth 310. The primary arc of the first tooth 305 may be compared to the secondary arc of the first tooth 305. The arc having the smaller radius of the two arcs may be selected as the minimum arc for the first tooth 305. Similarly, a minimum arc may be selected for the second tooth 305 by comparing the radius of the primary and secondary arcs of the second tooth 305. The minimum arc may be selected to ensure that the interdental filler model 315 does not protrude vertically outside of either the first tooth 305 or the second tooth 310.

Step 419: Determine a Series of Interpolated Arcs

Figure 20:
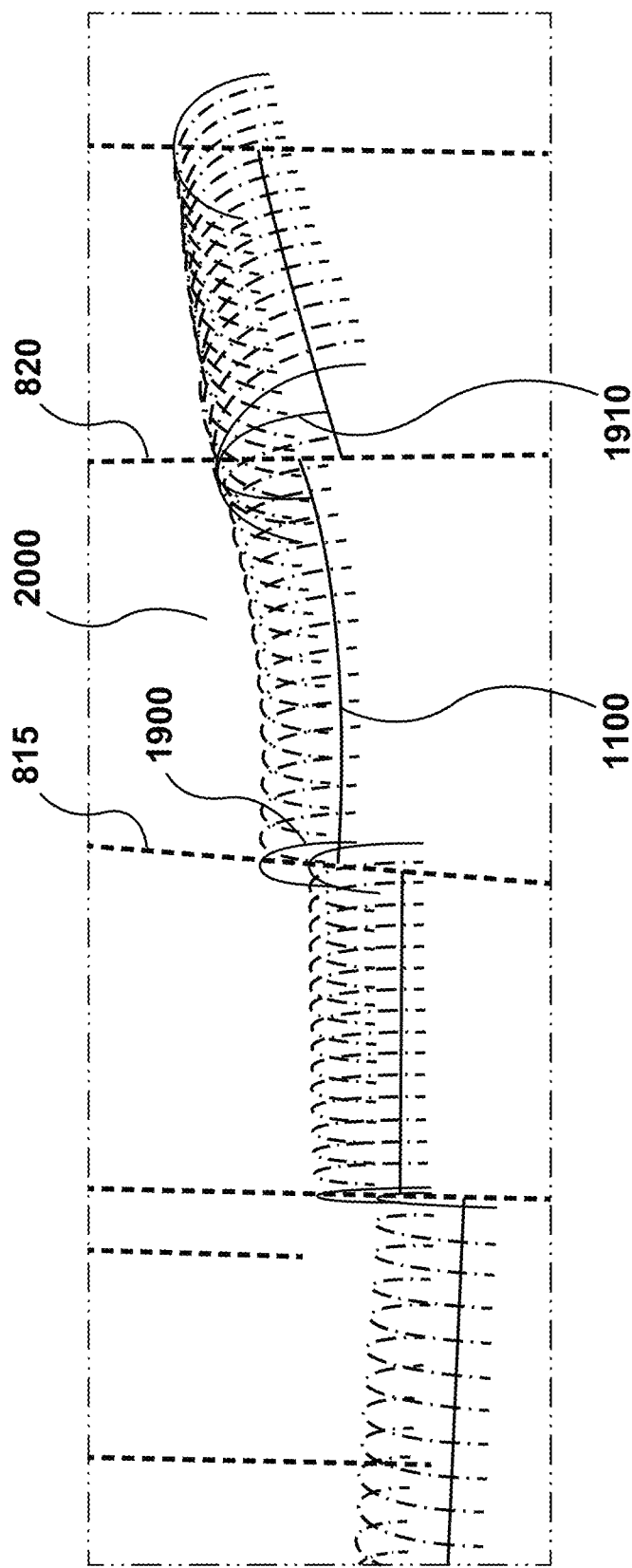
FIG. 20 shows an example of interpolated arcs according to non-limiting embodiments of the present technology.

At step 419, according to certain non-limiting embodiments of the present technology, the processor 110 may be configured to determine a series of interpolated arcs the first tooth 305 and the second tooth 305. The set of interpolated arcs may be interpolated between the minimum arcs selected at step 418. FIG. 20, described below, illustrates a set of interpolated arcs between teeth. The interpolated arcs may form the shape of the interdental filler model. An axial construction plane may be determined between the two minimum arcs, and then used to interpolate radii for each of the interpolated arcs.

Additionally, the processor 110 may be configured to use the construction arc determined at step 410 as a guide line for the interpolated arcs. The position of each arc of the interpolated arcs may be determined based on the construction arc. For example, a center of each interpolated arc may be positioned above the construction arc.

The number of interpolated arcs may be predetermined and/or selected by a user. For example, the number of interpolated arcs may be sixteen. If there are missing teeth, and the interdental gap is larger, the number of interpolated arcs may be increased, for example, up to 32.

The number of interpolated arcs may be determined based on the curvature of the construction arc, length of the construction arc, distance between the minimum arc of the first tooth 305 and the minimum arc of the second tooth 305, and/or the difference between the radii of the two minimum arcs. The determined number of interpolated arcs may be displayed to a user as a suggested number of interpolated arcs, and the user may then adjust the number of interpolated arcs.

Step 420: Extend the Interpolated Arcs

Figure 21:
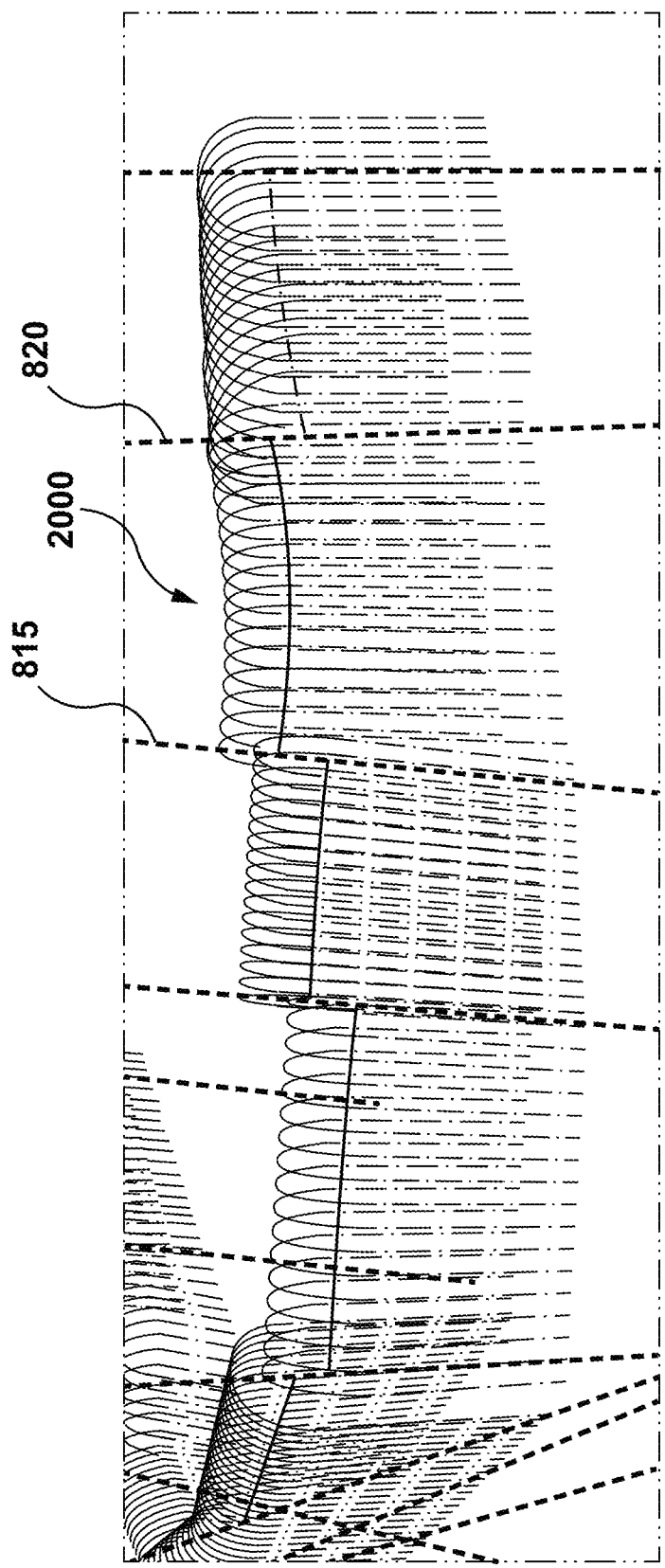
FIG. 21 shows an example of extended interpolated arcs according to non-limiting embodiments of the present technology.

At step 420, according to certain non-limiting embodiments of the present technology, the processor 110 may be configured to extend the interpolated arcs to end on a ground surface of the gingiva 220. FIG. 21, described below, illustrates a series of arcs that have been extended to end on a ground surface. Unlike the arc, which is curved, the extended portions may be a straight line. For each end of an arc, a corresponding point on the gingiva may be selected, and a straight line may be drawn from the end of the arc to the point on the gingiva.

Step 421: Connect Free Ends of the Interpolated Arcs

Figure 22:
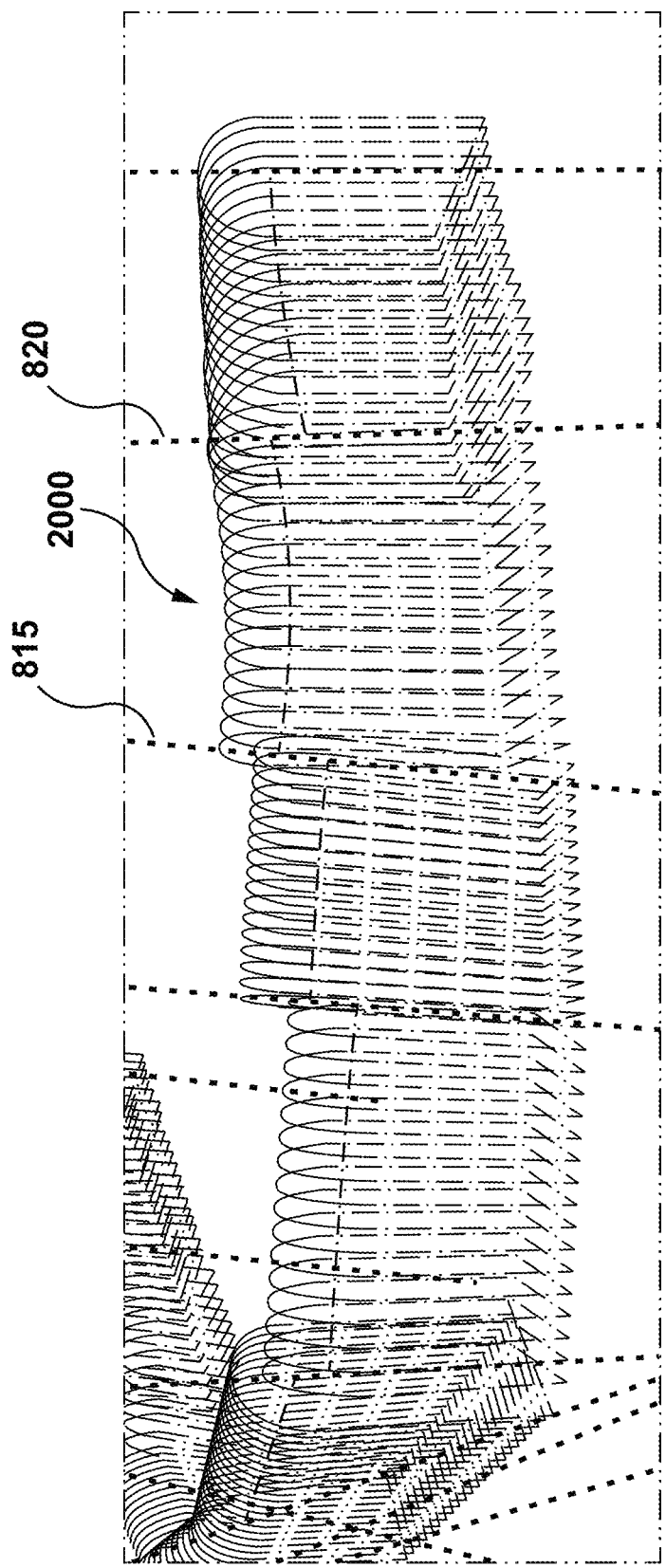
FIG. 22 shows an example of sections 2200 of an interdental filler model according to non-limiting embodiments of the present technology.

At step 421, according to certain non-limiting embodiments of the present technology, the processor 110 may be configured to connected free ends of the interpolated arcs. FIG. 22, described below, illustrates interpolated arcs with connected free ends. After step 420, each of the interpolated arcs may have two free ends. These two free ends may be on the gingiva 220, and may be the ends of the extended portions that were added at step 420. The two free ends for each interpolated arc may be connected by a straight line. After the free ends have been connected, each of the interpolated arcs may form a section of the interdental filler model.

Step 422: Generate the Interdental Filler Model

Figure 23:
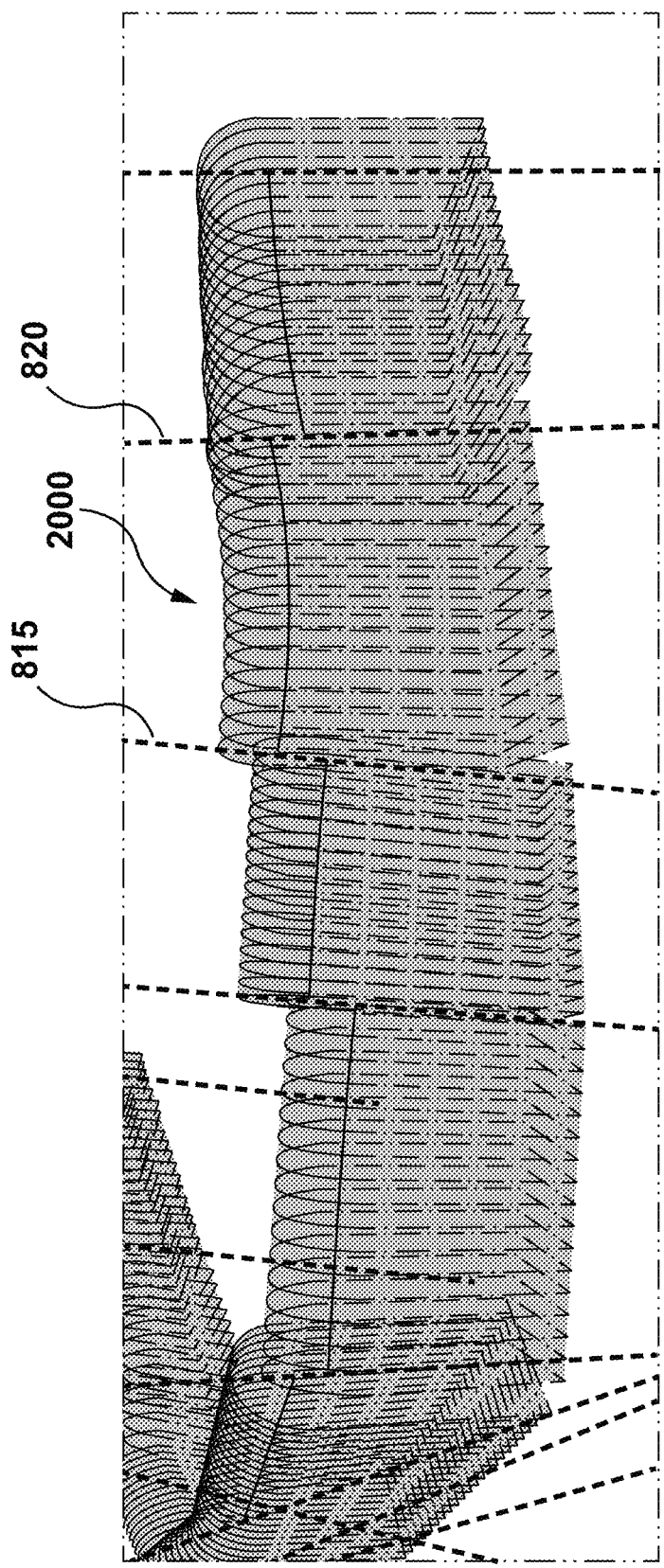
FIG. 23 shows an example of lofted sections 2300 of an interdental filler model according to non-limiting embodiments of the present technology.

At step 422, according to certain non-limiting embodiments of the present technology, the processor 110 may be configured to generate, based on the sections generated at step 421, a surface of the interdental filler model 315 using the sections as a supporting structure therefor, thereby, in a sense, lofting the sections to generate the interdental model filler 315. FIG. 23, described below, illustrates lofted sections. Each of the sections may be connected in series. The first and last sections in the series may be closed by a plane, thereby enclosing the interdental filler model 315. The interdental filler model 315 may then be displayed to and/or adjusted by a user.

According to certain non-limiting embodiments of the present technology, various parameters of the interdental filler model 315 may be adjusted by the user after the interdental filler model 315 has been generated and/or at any other time during generation of the interdental filler model 315. A bridge radius multiplier may be adjusted by the user. The bridge radius multiplier may multiply the radius of all arcs in the interdental filler model 315. This allows the user to increase or decrease the size of the interdental filler model 315. The bridge radius multiplier may be applied to a single interdental filler model and/or multiple interdental filler models. For example, multiple interdental filler models may be generated for the patient, and the same bridge radius multiplier may be applied to each of the interdental filler models for that patient.

Further, according to certain non-limiting embodiments of the present technology, the processor 110 may be configured to superimpose the interdental filler model 315 with the archform mesh 200 and cause display thereof to the user.

Also, in some non-limiting embodiments of the present technology, a bridge height delta value may be adjusted by the user. The bridge height delta value may be an amount to shift all arc centers by along the y-axis of the axial construction planes. The user may increase or decrease the height of the interdental filler model by adjusting the bridge height delta value. The bridge height delta value may be applied to a single interdental filler model and/or multiple interdental filler models.

In some non-limiting embodiments of the present technology, a construction arc bend value may be adjusted by the user to adjust the shape of the interdental filler model. The construction arc bend value may represent a distance between a mid-point of the construction arc determined at step 410 and the center point of the construction line determined at step 407.

In some non-limiting embodiments of the present technology, a minimum arc radius multiplier may be adjusted by the user. The minimum arc multiplier may be used to increase and/or decrease the radius of the minimum arcs selected at step 418 and used to generate the interdental filler model. The radius of the minimum arcs on either side of the interdental filler model may be adjusted, and/or the radii of both minimum arcs may be adjusted. The user may select which side of the interdental filler model the user wishes to adjust, such as by selecting the first tooth 305 or the second tooth 305, and then the user may adjust the minimum arc radius corresponding to that side.

In some non-limiting embodiments of the present technology, a minimum arc height delta may be adjusted by the user. The user may select which side of the interdental filler model the user wishes to adjust, and then cause the minimum arc corresponding to the selected tooth to be shifted along the Y-axis of the axial construction plane.

Step 423: Manufacture the Interdental Filler

At step 423, according to certain non-limiting embodiments of the present technology, the processor 110 may be configured to cause manufacturing the interdental filler based on the interdental filler model 315. The interdental filler may be manufactured as a stand-alone orthodontic appliance, or the interdental filler may be integrated within another orthodontic appliance. For example, the interdental filler may be formed as part of an aligner. If the interdental filler is formed as part of an orthodontic appliance, the interdental filler model 315 may be merged with a model of the orthodontic appliance. The interdental filler model 315 may be used for further modeling, such as to determine thickness of the orthodontic appliance after thermoforming.

In some non-limiting embodiments of the present technology, the processor 110 may be configured to determine the thickness of the orthodontic appliance using one or more approaches described in a co-owned U. S. patent application Ser. No. 17/143,074, filed on Jan. 6, 2021, concurrently with the present application, the present application, entitled "SYSTEMS AND METHODS FOR FORMING DENTAL APPLIANCES"; the content of which is hereby incorporated by reference in its entirety.

In additional non-limiting embodiments of the present technology, the superimposed 3D model of the archform mesh 200 and the interdental filler model 315 may be used for producing the mold of the patient's archform representative of the desired configuration thereof; and the processor 110 may be configured to cause manufacturing the orthodontic appliance based on the mold. As a result, portions of the orthodontic appliance thus produced associated with the interdental gap may extend, between the first tooth 305 and the second tooth 310, over the patient's gingiva, when the orthodontic appliance is worn over the patient's teeth, and may thus not cause additional discomfort to the patient.

In some non-limiting embodiments of the present technology, the manufacturing the orthodontic appliance may comprise the thermoforming on the so-produced mold, the processor 110 may be further configured to determine a cut line used for cutting an unfinished aligner after the thermoforming, thereby forming the orthodontic appliance. In specific non-limiting embodiments of the present technology, the processor 110 may be configured to determine the cut line using one of the approaches described in a co-owned U.S. Pat. No. 11,058,515 issued on Jul. 13, 2021, entitled "SYSTEMS AND METHODS FOR FORMING DENTAL APPLIANCES"; the content of which is hereby incorporated by reference in its entirety.

Archform with Construction Lines

FIG. 8 shows an example of an archform with construction lines determined by the processor 110, according to non-limiting embodiments of the present technology. Two intersection lines between the teeth 230 and the gingiva 220 are shown, a first intersection line 805 corresponding to the first tooth 305 and a second intersection line 810 corresponding to the second tooth 305. The first intersection line 805 and the second intersection line 810 indicate the boundaries between the first tooth 305 and the second tooth 310 and the gingiva 220. In some non-limiting embodiments of the present technology, the processor 110 may be configured to determine the first intersection line 805 and the second intersection line 810 as described above in respect of step 402 of the method 400.

A first tooth axis 815 corresponds to the first tooth 305 and a second tooth axis 820 corresponds to the second tooth 305. In some non-limiting embodiments of the present technology, the processor 110 may be configured to determine the first tooth axis 815 and the second tooth axis 820 as described above in respect of step 403 of the method 400. A first intersection point 825 corresponds to the first tooth 305 and a second intersection point 830 corresponds to the second tooth 305. The first intersection point 825 is on the first intersection line 805, and the second intersection point 830 is on the second intersection line 810. In some non-limiting embodiments of the present technology, the processor 110 may be configured to determine the first intersection point 825 and the second intersection point 830 as described above at step 405 of the method 400.

As it can be appreciated, a construction line 835 connects the first intersection point 825 and the second intersection point 830. The construction line 835 may be a straight line extending between the first intersection point 825 and the second intersection point 830. In some non-limiting embodiments of the present technology, the processor 110 may be configured to determine the construction line 835 as described above at step 406 of the method 400.

Archform with Construction Centers

Figure 9:
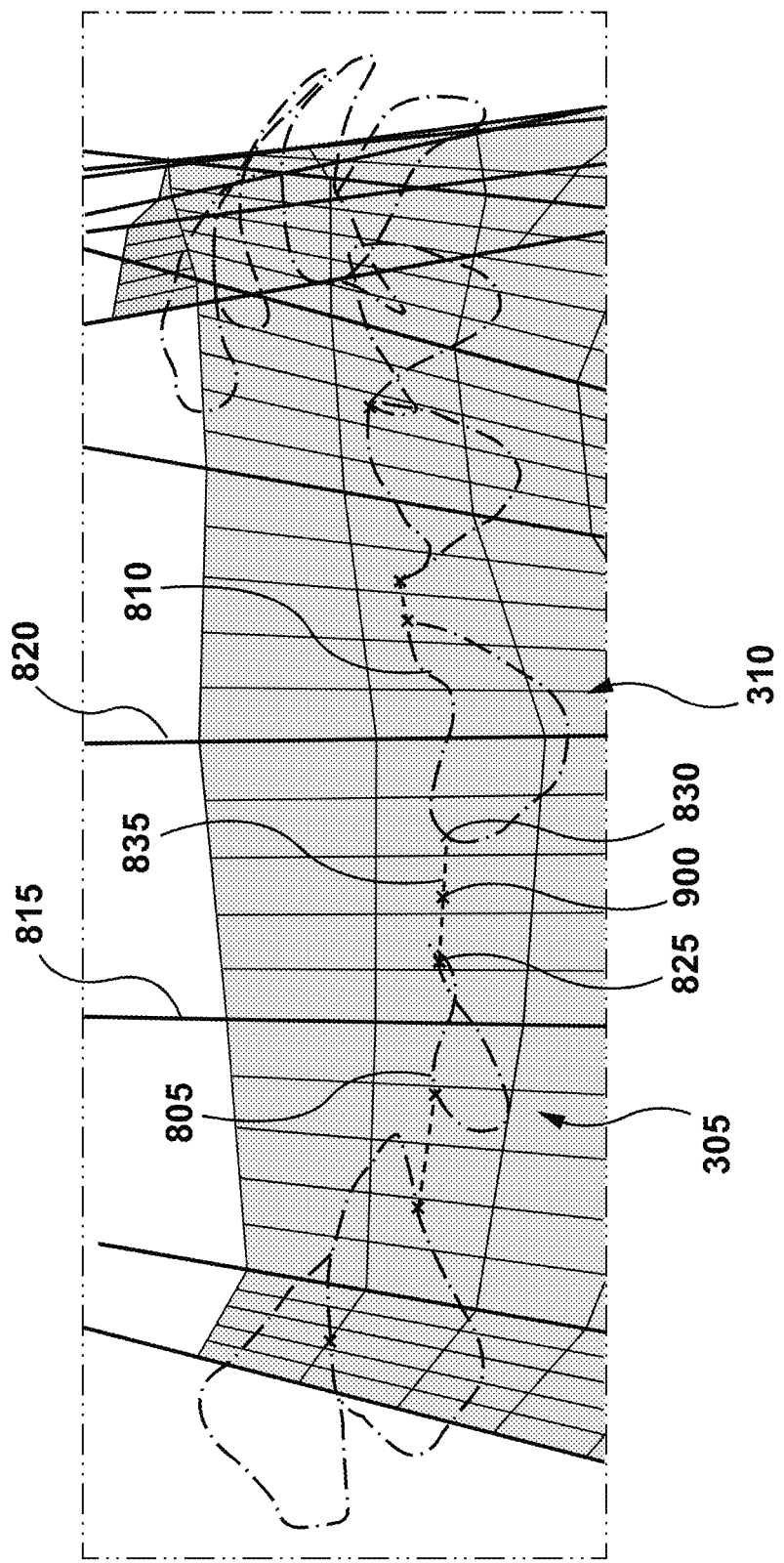
FIG. 9 shows an example of an archform with construction centers according to non-limiting embodiments of the present technology.

FIG. 9 shows an example of an archform with construction centers determined by the processor 110, according to non-limiting embodiments of the present technology. After determining the construction line 835, the processor 110 may be configured to determine a construction center 900. The construction center 900 may be a center of the construction line 835. The construction center 900 may be equidistant from the first intersection point 825 of the first tooth 305 and the second intersection point 830 of the second tooth 305. In some non-limiting embodiments of the present technology, the processor 110 may be configured to determine the construction center 900 as described above at step 407 of the method 400.

Closest Vertices

FIG. 10 shows an example of closest vertices determined by the processor 110, according to non-limiting embodiments of the present technology. After determining the construction center 900, the processor 110 may be configured to determine a first closest vertex 1010 corresponding to the first tooth 305 and/or a second closest vertex 1020 corresponding to the second tooth 305. The first closest vertex 1010 may be a vertex on the first tooth axis 815 that is closest, of all vertices on the first tooth axis 815, to the construction center 900. Similarly, the second closest vertex 1020 may be a vertex on the second tooth axis 820 that is closest to the construction center 900. In some non-limiting embodiments of the present technology, the processor 110 may be configured to determine the first closest vertex 1010 and the second closest vertex 1020 as described above at steps 408 and 409 of the method 400.

Construction Arcs

FIG. 11 shows an example of construction arcs determined by the processor 110, according to non-limiting embodiments of the present technology. After determining the construction center 900, first closest vertex 1010, and second closest vertex 1020, the processor 110 may be configured to determine a construction arc 1100. The construction arc 1100 may be a three point arc connecting the first closest vertex 1010, construction center 900, and second closest vertex 1020. A curvature of the construction arc 1100 may be adjusted manually by a user, such as by adjusting the location of the construction center 900. In some non-limiting embodiments of the present technology, the processor 110 may be configured to determine the construction arc 1100 as described above at step 410 of the method 400.

Construction Arc Tangent Vectors

FIG. 12 shows an example of construction arc tangent vectors determined by the processor 110, according to non-limiting embodiments of the present technology. First tangent vector 1200 and second tangent vector 1200 may be determined at either end of the construction arc 1100. The first tangent vector 1200 may begin at the first closest vertex 1010. The second tangent vector 1200 may begin at the second closest vertex 1020. The first tangent vector 1200 and second tangent vector 1200 may have any length.

Axial Construction Planes

FIG. 13 shows an example of axial construction planes determined by the processor 110, according to non-limiting embodiments of the present technology. First axial construction plane 1300 corresponds to the first tooth 305 and second axial construction plane 1310 corresponds to the second tooth 305. The first axial construction plane 1300 may be generated based on the first closest vertex 1010, first tooth axis 815, and the first tangent vector 1200. Similarly, the second axial construction plane 1310 may be generated based on the second closest vertex 1020, second tooth axis 820, and the second tangent vector 1200.

The center of the first axial construction plane 1300 may be the first closest vertex 1010. The x-axis of the first axial construction plane 1300 may be the cross product of the first tooth axis 815 and the first tangent vector 1200. The y-axis of the first axial construction plane 1300 may be the first tooth axis 815. Similarly, the center of the second axial construction plane 1310 may be the second closest vertex 1020. The y-axis of the second axial construction plane 1310 may be the second tooth axis 820. The x-axis of the second axial construction plane 1310 may be the cross product of the second tooth axis 820 and the second tangent vector 1200. In some non-limiting embodiments of the present technology, the processor 550 may be configured to determine the first axial construction plane 1300 and the second axial construction plane 1310 as described above at step 411 of the method 400.

Curves of Intersection

FIG. 14 shows an example of curves of intersection determined by the processor 110, according to non-limiting embodiments of the present technology. A first curve of intersection 1400 indicates the intersection between the first axial construction plane 1300 and the mesh of the first tooth 305. A second curve of intersection 1410 indicates the intersection between the second axial construction plane 1310 and the mesh of the second tooth 305. The curves of intersection 1400 and 1410 may trace the surfaces of the first tooth 305 and the second tooth 310. In some non-limiting embodiments of the present technology, the processor 110 may be configured to determine the first curve of intersection 1400 and the second curve of intersection 1410 as described above at step 412 of the method 400.

Portion of Curves of Intersection

FIG. 15 shows an example of portions of the curves of intersection generated by the processor 110, according to non-limiting embodiments of the present technology. At least one of the first curve of intersection 1400 and the second curve of intersection 1410 may be shortened. The portion of the first curve of intersection 1400 that is below the first intersection line 805 may be removed. A first curve 1500 may be the resulting portion of the first curve of intersection 1400 after removing the portion below the first intersection line 805. Similarly, a second curve 1510 may be the resulting portion of the second curve of intersection 1410 after removing the portion below the second intersection line 810. In some non-limiting embodiments of the present technology, the first curve 1500 and the second curve 1510 as described above at step 413 of the method 400.

Distances on Curve of Intersection

FIG. 16 shows an example of distances on a curve of intersection according to non-limiting embodiments of the present technology. For various points on the second curve 1510, a distance is determined between each point and the second closest vertex 1020. FIG. 16 illustrates the distances determined for points on the second curve 1510. The processor 110 may be configured to determine a given point 1600 on the second curve 1510 having the shortest distance to the second closest vertex 1020. The distance between the given point 1600 and the second closest vertex 1020 may then be used to determine an arc radius for a primary arc. Although FIG. 16 illustrates determining this distance for a single tooth (the second tooth 305), it should be understood that a shortest distance may be found for each tooth at either end of the interdental gap, such as for both the first tooth 305 and the second tooth 310. The processor 110 may be configured to determine the shortest distances for each tooth as described above at step 414 of the method 400.

Primary Arcs

FIG. 17 shows an example of primary arcs generated by the processor 110, according to non-limiting embodiments of the present technology. For example, the processor 110 may be configured to generate a first primary arc 1700 may be determined for the first tooth 305 and a second primary arc 1710 may be determined for the second tooth 305. The radius of the second primary arc 1710 may be determined based on the distance illustrated in FIG. 16 between the point 1600 and the second closest vertex 1020. The center of the first primary arc 1700 may be in the first axial construction plane 1300. The center of the second primary arc 1710 may be in the second axial construction plane 1310. In some non-limiting embodiments of the present technology, the processor 110 may be configured to determine the first primary arc 1700 and the second primary arc 1710 as described above at step 415 of the method 400.

Secondary Radius

FIG. 18 shows an example of points used by the processor 110 to determine a secondary radius, according to non-limiting embodiments of the present technology. For example, the processor 110 may be configured to determine a first circle 1800 for the first tooth 305, and a second circle 1810 for the second tooth 305. The radius of the first circle 1800 may be used to generate a secondary arc for the first tooth 305 and/or a radius of the second circle 1810 may be used to generate a secondary arc for the second tooth 305. In some non-limiting embodiments of the present technology, the processor 110 may be configured to determine the radius of the first circle 1800 and the radius of the second circle 1810 as described above in respect of the secondary radii determined at step 416 of the method 400.

To generate the first circle 1800, the processor 110 may further be configured to determine a set of equally distributed points on the first intersection line 805. Any number of distributed points may be used. For example, the processor 110 may be configured to determine an arithmetic average of the distributed points for the distributed points on the first intersection line 805. The arithmetic average of the distributed points may be used as a center of the first circle 1800.

Further, the processor 110 may be configured to determine a best fitting plane of the distributed points on the first intersection line 805. For example, the processor 110 may be configured to use the plane of the first circle 1800 as the best fitting plane. Each of the distributed points may be projected on the best fitting plane. Finally, the processor 110 may be configured to determine the radius of the first circle 1800 as a mean distance between the projected points and the center of the first circle 1800 as. The processor 110 may then be configured to generate the first circle 1800 using the determined circle center, best fitting plane, and radius. Similar to the first tooth 305, the processor 110 may be configured to determine a secondary radius for the second tooth 305 based on a set of distributed points on the second intersection line 810.

Secondary Arcs

Figure 19:
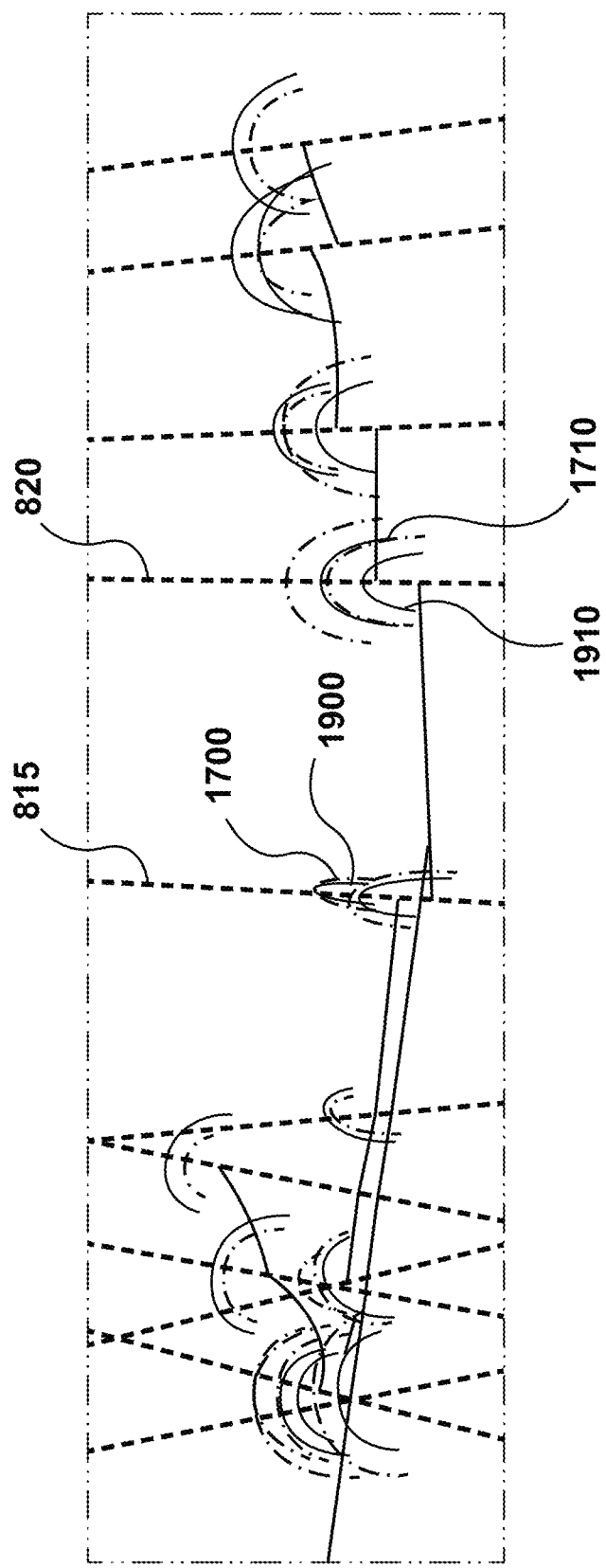
FIG. 19 shows an example of secondary arcs according to non-limiting embodiments of the present technology.

FIG. 19 shows an example of secondary arcs determined by the processor 110, according to non-limiting embodiments of the present technology. For example, the processor 110 may be configured to determine a first secondary arc 1900 for the first tooth 305 and a second secondary arc 1910 for the second tooth 305. In some non-limiting embodiments of the present technology, the processor 110 may be configured to determine a radius of the first secondary arc 1900 based on the radius of the first circle 1800. For example, the radius of the first secondary arc 1900 may be half the radius of the first circle 1800. Similarly, a radius of the second secondary arc 1910 may be determined based on the second circle 1810.

The processor 110 may be configured to generate the first secondary arc 1900 and the second secondary arc 1910 similar to the primary arcs 1700 and 1710, except that the radius of the first primary arc 1700 may be different from the radius of the first secondary arc 1900 and the radius of the second primary arc 1710 may be different from the radius of the second secondary arc 1910. In some non-limiting embodiments of the present technology, the processor 110 may be configured to generate the first secondary arc 1900 and the second secondary arc 1910 as described above at step 417 of the method 400.

Further, the processor 110 may be configured to select, for example, for the first tooth 305, either the first primary arc 1700 or the first secondary arc 1900 to be used for generating the interdental filler model 315. For example, in some non-limiting embodiments of the present technology, the processor 110 may be configured to select one of the first primary arc 1700 and the first secondary arc 1900 having the smaller radius. In FIG. 19, the first secondary arc 1900 has a smaller radius than the first primary arc 1700, so the processor 110 may be configured to select the first secondary arc 1900. Similarly, the second secondary arc 1910 has a smaller radius than the second primary arc 1710, so the second secondary arc 1910 may thus be selected by the processor 110. In some non-limiting embodiments of the present technology, the processor 110 may be configured to execute the selection procedure as described above at step 418 of the method 400.

Interpolated Arcs

FIG. 20 shows an example of interpolated arcs generated by the processor 110, according to non-limiting embodiments of the present technology. For example, the processor 110 may be configured to determine a set of interpolated arcs 2000 between the first secondary arc 1900 and second secondary arc 1910. Although FIG. 20 illustrates the set of interpolated arcs 2000 being interpolated between two secondary arcs, it should be noted that in various non-limiting embodiments of the present technology, the set of interpolated arcs 2000 may be generated between a given pair of secondary arcs, a given pair of primary arcs, or one primary arc and one secondary arc, as an example.

The set of interpolated arcs 2000 trace the construction arc 1100. Thus, in some non-limiting embodiments of the present technology, the processor 110 may be configured to determine a respective center of each of the set of interpolated arcs 2000 based on the construction arc 1100. Further, the processor 110 may be configured to determine a number of interpolated arcs in the set of interpolated arcs 2000 based on the curvature of the construction arc 1100, distance between the first secondary arc 1900 and second secondary arc 1910, and/or the difference between the radius of the first secondary arc 1900 and the radius of the second secondary arc 1910. The number of interpolated arcs in the set of interpolated arcs 2000 may be pre-determined and/or adjusted by a user. In some non-limiting embodiments of the present technology, the processor 110 may be configured to determine the set of interpolated arcs 2000 as described above at step 419 of the method 400.

Extended Interpolated Arcs

FIG. 21 shows an example of extended interpolated arcs generated by the processor 110, according to non-limiting embodiments of the present technology. As mentioned above, the processor 110 may be configured to extend each arc in the set of interpolated arcs 2000 to end on a ground surface, such as the gingiva 220. FIG. 21 illustrates the set of interpolated arcs 2000 with extensions to end on the gingiva 220. In some non-limiting embodiments of the present technology, the extended portions may be straight lines stretching from ends of each one of the set of interpolated arcs 2000 to the gingiva 220. In some non-limiting embodiments of the present technology, the processor 110 may be configured to generate the extended interpolated arcs as described at step 420 of the method 400.

Sections of an Interdental Filler Model

FIG. 22 shows an example of sections 2200 of the interdental filler model 315 generated by the processor 110, according to non-limiting embodiments of the present technology. According to certain non-limiting embodiments of the present technology, the processor 110 may be configured to connect the free ends of the extended interpolated arcs illustrated in FIG. 21 to form sections 2200. Each section of the sections 2200 may correspond to a respective arc of the set of interpolated arcs 2000. According to some non-limiting embodiments of the present technology, the processor 110 may be configured to generate the sections 2200 as described at step 421 of the method 400.

Lofted Sections

FIG. 23 shows an example of lofted sections 2300 of the interdental filler model 315, according to non-limiting embodiments of the present technology. According to certain non-limiting embodiments of the present technology, the processor 110 may be configured to loft the sections 2200 to form the lofted sections 2300. To that end, the processor 110 may be configured to connect each of the sections 2200 in series. As it may become apparent, a first section and a last section of the sections 2200 may be enclosed by a plane. Thus, by generating the lofted sections 2300, the processor 110 may be configured to generate the interdental filler model 315 between the first tooth 305 and the second tooth 310. In some non-limiting embodiments of the present technology, the processor 110 may be configured to generate the lofted sections 2300 as described above at step 422 of the method 400.

Interdental Filler Model

Figure 24:
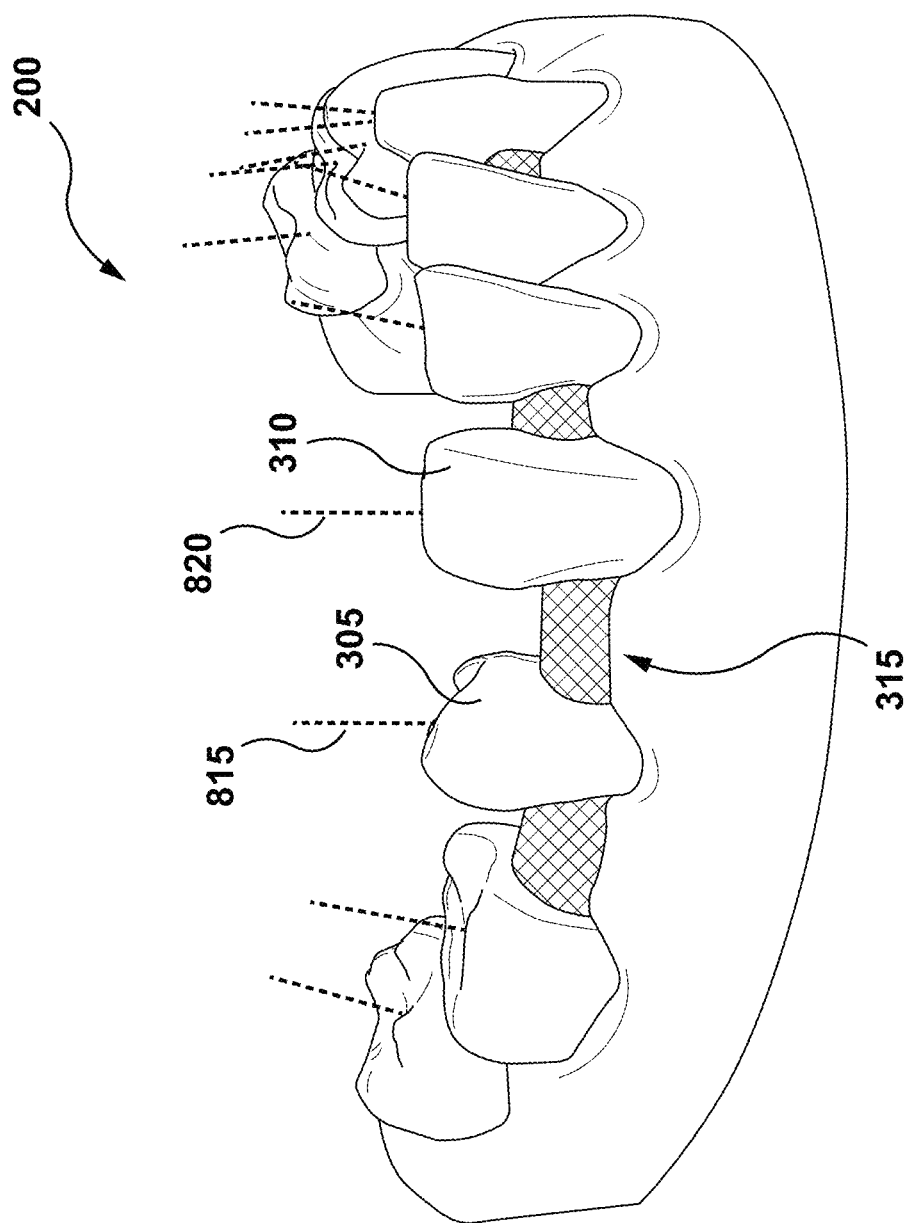
FIG. 24 shows an example of an interdental filler model 2400 according to non-limiting embodiments of the present technology.

FIG. 24 shows an example of the interdental filler model 315 generated by the processor 110, according to non-limiting embodiments of the present technology. The interdental filler model 315 may be formed using the lofted sections 2300. The interdental filler model 315 may fill the interdental gap between the first tooth 305 and the second tooth 305. According to certain non-limiting embodiments of the present technology, the processor 110 may be configured to generate the interdental filler model 315 as described above at step 422 of the method 400. Further, the processor 110 may be configured to cause manufacturing of the interdental filler based on the interdental filler model 315 as described above at step 423 of the method 400.

As mentioned above, the interdental filler model 315 may be used to generate an interdental filler used as a separate orthodontic device, such as a part of the orthodontic appliance providing support thereto within the interdental gap between the first tooth 305 and the second tooth 310. In other non-limiting embodiments of the present technology, the archform mesh 200 including the interdental filler model 315 may be used for manufacturing the mold of the patient's archform for further producing the orthodontic appliance. According to some non-limiting embodiments of the present technology, the orthodontic appliance thus produced may be free of contact with the patient's gingiva when worn on the patient's teeth due to portions thereof associated with the interdental gap would reproduce the interdental filler model 315. Such an orthodontic appliance, according to some non-limiting embodiments of the present technology, may allow for an improved comfort of using it by the patient, which may consequently increase patient's adherence to the orthodontic treatment.

While the above-described implementations have been described and shown with reference to particular steps performed in a particular order, it will be understood that these steps may be combined, sub-divided, or re-ordered without departing from the teachings of the present technology. At least some of the steps may be executed in parallel or in series. Accordingly, the order and grouping of the steps is not a limitation of the present technology.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to be exemplary rather than limiting.

What is claimed is:

1. A method for generating an interdental filler model for a patient, wherein the interdental filler model is configured to fill an interdental gap between a first tooth and a second tooth of the patient, wherein the first tooth and the second tooth are neighboring teeth, the method executable by a processor of a computing system, the method comprising:
   receiving a three-dimensional (3D) digital model of an archform of the patient, wherein the 3D digital model comprises a representation of gingiva and a plurality of teeth including the first tooth and the second tooth;
   determining locations for ends of the interdental filler model by:
      determining a first vertex on a tooth axis of the first tooth, and
      determining a second vertex on a tooth axis of the second tooth;
   determining a curvature of the interdental filler model by:
      determining a first arc connecting the first vertex to the second vertex;
   determining a shape of the interdental filler model by:
      determining a second arc having a center at the first vertex,
      determining a third arc having a center at the second vertex, and
      interpolating a set of arcs between the second arc and the third arc, wherein a geometric center of each arc in the set of arcs corresponds to a vertex on the first arc, wherein the first arc does not lie on any arc in the set of arcs, and wherein each arc in the set of arcs is disconnected from the second arc and the third arc;
   grounding the interdental filler model on the gingiva by:
      extending each arc of the set of arcs to end on a ground surface; and
   generating the interdental filler model by:
      connecting free ends of each arc of the set of arcs, thereby forming a set of sections, and
      forming the interdental filler model by connecting the set of sections to form a surface enclosing the interdental filler model.

2. The method of claim 1, wherein determining the locations for ends of the interdental filler model comprises:
   determining a third vertex corresponding to the first tooth;
   determining a fourth vertex corresponding to the second tooth; and
   determining a center point of a line connecting the third vertex and the fourth vertex, wherein the first arc comprises the center point.

3. The method of claim 2, wherein determining the first vertex comprises determining a nearest vertex on the tooth axis of the first tooth to the center point.

4. The method of claim 2, wherein determining the third vertex comprises determining a highest or lowest vertex of the first tooth.

5. The method of claim 1, wherein determining the shape of the interdental filler model comprises:
   determining, based on the tooth axis of the first tooth, a first plane comprising the first vertex;
   determining, based on the tooth axis of the second tooth, a second plane comprising the second vertex;
   determining a first intersection curve, wherein the first intersection curve comprises a boundary line between the first tooth and the first plane;
   determining a second intersection curve, wherein the second intersection curve comprises a boundary line between the second tooth and the second plane;
   determining a first distance from a point on the first intersection curve to the first vertex; and
   determining a second distance from a point on the second intersection curve to the second vertex.

6. The method of claim 5, wherein the second arc has a radius less than the first distance, and wherein the third arc has a radius less than the second distance.

7. The method of claim 5, further comprising determining a tangent vector to the first arc at the first vertex.

8. The method of claim 7, wherein a first axis of the first plane is a cross product of the tangent vector and the tooth axis of the first tooth.

9. The method of claim 8, wherein a second axis of the first plane is the tooth axis of the first tooth.

10. The method of claim 1, further comprising manufacturing, based on the interdental filler model, an orthodontic appliance for the patient, wherein the orthodontic appliance includes a portion corresponding to the interdental filler model to fill the interdental gap between the first tooth and the second tooth.

11. The method of claim 1, further comprising manufacturing, based on the interdental filler model an interdental filler for the patient.

12. The method of claim 1, wherein determining the locations for ends of the interdental filler model comprises determining the tooth axis of the first tooth and the tooth axis of the second tooth.

13. The method of claim 1, further comprising causing display of the interdental filler model.

14. The method of claim 13, further comprising superimposing the interdental filler model on the 3D digital model of the archform of the patient.

15. The method of claim 1, further comprising determining, based on a curvature of the first arc, a number of arcs to interpolate between the second arc and the third arc.

16. A system comprising:
   at least one processor, and
   memory storing a plurality of executable instructions which, when executed by the at least one processor, cause the system to:
   receive a three-dimensional (3D) digital model of an archform of the patient, wherein the 3D digital model comprises a representation of gingiva and a plurality of teeth including a first tooth and a second tooth that are neighboring teeth;
   determine locations for ends of an interdental filler model configured to fill an interdental gap between the first tooth and the second tooth by:
      determining a first vertex on a tooth axis of the first tooth, and
      determining a second vertex on a tooth axis of the second tooth;
   determine a curvature of the interdental filler model by:
      determining a first arc connecting the first vertex to the second vertex;
   determine a shape of the interdental filler model by:
      determining a second arc having a center at the first vertex,
      determining a third arc having a center at the second vertex, and interpolating a set of arcs between the second arc and the third arc, wherein a geometric center of each arc in the set of arcs corresponds to a vertex on the first arc, wherein the first arc does not lie on any arc in the set of arcs, and wherein each arc in the set of arcs is disconnected from the second arc and the third arc;

ground the interdental filler model on the gingiva by:
extending each arc of the set of arcs to end on a ground surface; and generate the interdental filler model by:
connecting free ends of each arc of the set of arcs, thereby forming a set of sections, and
forming the interdental filler model by connecting the set of sections to form a surface enclosing the interdental filler model.

17. The system of claim 16, wherein the instructions, when executed by the at least one processor, cause the system to manufacture, based on the interdental filler model, an orthodontic appliance for the patient, wherein the orthodontic appliance includes a portion corresponding to the interdental filler model to fill the interdental gap between the first tooth and the second tooth.

18. The system of claim 16, wherein the instructions, when executed by the at least one processor, cause the system to manufacture, based on the interdental filler model an interdental filler for the patient.

19. The system of claim 16, wherein the instructions, when executed by the at least one processor, cause the system to cause display of the interdental filler model.

20. The system of claim 19, wherein the instructions, when executed by the at least one processor, cause the system to superimpose the interdental filler model on the 3D digital model of the archform of the patient.

* * * * *